(12) United States Patent
Bjornebo et al.

(10) Patent No.: US 10,407,296 B2
(45) Date of Patent: Sep. 10, 2019

(54) OPTICAL FLUID SENSORS FOR CROSS CONTAMINATION CONTROL SYSTEMS

(71) Applicant: Knappco Corporation, Kansas City, MO (US)

(72) Inventors: Erik Paul Bjornebo, Kansas City, MO (US); Jeffrey Joseph Blair, Kansas City, MO (US); Mark William Dudley, Smithville, MO (US); Richard Lee Henderson, Leawood, KS (US)

(73) Assignee: KNAPPCO CORPORATION, Kansas City, MO (US)

( * ) Notice: Subject to any disclaimer, the term of this patent is extended or adjusted under 35 U.S.C. 154(b) by 188 days.

(21) Appl. No.: 15/291,178

(22) Filed: Oct. 12, 2016

(65) Prior Publication Data

US 2018/0099860 A1 Apr. 12, 2018

(51) Int. Cl.
*G01N 33/22* (2006.01)
*B67D 7/34* (2010.01)
(Continued)

(52) U.S. Cl.
CPC ............ *B67D 7/342* (2013.01); *G01N 21/59* (2013.01); *G01N 21/645* (2013.01); *G01N 21/85* (2013.01);
(Continued)

(58) Field of Classification Search
CPC ................................ G01N 21/85; G01N 33/22
See application file for complete search history.

(56) References Cited

U.S. PATENT DOCUMENTS

| 4,469,149 A | 9/1984 | Walkey et al. |
| 4,838,323 A | 6/1989 | Watts |

(Continued)

FOREIGN PATENT DOCUMENTS

| AU | 2007200878 A1 | 9/2007 |
| EP | 0568837 A2 | 4/1993 |

(Continued)

OTHER PUBLICATIONS

Alfons Haar, SPDS—Sealed Parcel Delivery System, "Automatic recognition of tampering: No additional analysis of report data in the office"; [online]. Retrieved from the Internet: www.alfons-haar.de.; (2 pages).

(Continued)

*Primary Examiner* — Kevin F Murphy
(74) *Attorney, Agent, or Firm* — Dinsmore & Shohl LLP

(57) ABSTRACT

An optical fluid sensor (OFS) is disclosed that includes a body defining a chamber and having one or more apertures to allow a fluid to enter the chamber, a light source optically coupled to the chamber and configured to emit light into the chamber, and a detector optically coupled to the chamber and configured to receive light from the chamber. The light source may emit IR, visible, and UV light into the chamber, and the detector may measure an intensity of one or more wavelengths of IR or visible light received by the detector. When fluid is disposed within the chamber, the light emitted by the light source may pass into and through the fluid disposed in the chamber before being received by the detector. A crossover protection system is also disclosed that includes an OFS for determining a transported liquid type.

26 Claims, 16 Drawing Sheets

(51) Int. Cl.
*G01N 21/59* (2006.01)
*G01N 21/64* (2006.01)
*G01N 21/85* (2006.01)

(52) U.S. Cl.
CPC ......... *G01N 21/8507* (2013.01); *G01N 33/22* (2013.01); *G01N 2201/062* (2013.01); *G01N 2201/12* (2013.01)

(56) References Cited

U.S. PATENT DOCUMENTS

| | | | |
|---|---|---|---|
| 5,094,517 | A | 3/1992 | Franke |
| 5,187,366 | A | 2/1993 | Hopenfeld |
| 5,209,275 | A | 5/1993 | Akiba et al. |
| 5,309,957 | A | 5/1994 | Saisuu |
| 5,349,994 | A | 9/1994 | Koeninger |
| 5,460,210 | A | 10/1995 | Koeninger |
| 5,507,326 | A | 4/1996 | Cadman et al. |
| 5,515,890 | A | 5/1996 | Koeninger |
| 5,604,681 | A | 2/1997 | Koeninger |
| 5,605,182 | A | 2/1997 | Oberrecht et al. |
| 5,654,497 | A | 8/1997 | Hoffheins et al. |
| 5,655,577 | A | 8/1997 | Loen et al. |
| 5,722,469 | A | 3/1998 | Tuminaro |
| 6,244,287 | B1 | 6/2001 | Hill et al. |
| 6,341,629 | B1 | 1/2002 | Clark et al. |
| 6,347,723 | B1 | 2/2002 | Barlian et al. |
| 6,394,150 | B1 | 5/2002 | Haimovich et al. |
| 6,616,036 | B2 | 9/2003 | Streicher et al. |
| 6,622,758 | B2 | 9/2003 | Drube et al. |
| 6,649,829 | B2 | 11/2003 | Garber et al. |
| 6,678,052 | B1 * | 1/2004 | Hanagandi ............ G01N 21/85 356/410 |
| 6,897,374 | B2 | 5/2005 | Garber et al. |
| 7,012,536 | B2 | 3/2006 | McConnel et al. |
| 7,188,771 | B2 | 3/2007 | Poulter |
| 7,414,244 | B2 * | 8/2008 | Minamiura .......... G01N 21/314 250/338.1 |
| 7,628,182 | B2 | 12/2009 | Poulter et al. |
| 7,647,954 | B2 | 1/2010 | Garber et al. |
| 7,656,533 | B2 | 2/2010 | Kang et al. |
| 7,672,544 | B2 | 3/2010 | Takabayashi et al. |
| 7,859,662 | B2 | 12/2010 | Hamatani et al. |
| 7,911,595 | B2 * | 3/2011 | Serai ................. G01J 3/10 356/70 |
| 8,261,784 | B2 | 9/2012 | Gerard et al. |
| 8,295,657 | B2 | 10/2012 | Mitani et al. |
| 8,593,290 | B2 | 11/2013 | Hunter et al. |
| 2007/0198186 | A1 | 8/2007 | Realini et al. |
| 2011/0040503 | A1 | 2/2011 | Rogers et al. |
| 2011/0120589 | A1 | 5/2011 | Evans |
| 2012/0158192 | A1 | 6/2012 | Sherwood |
| 2013/0283893 | A1 | 10/2013 | Earl et al. |
| 2014/0129038 | A1 | 5/2014 | Finnell et al. |
| 2014/0316589 | A1 | 10/2014 | Lichtash |
| 2016/0076995 | A1 | 3/2016 | Coates et al. |

FOREIGN PATENT DOCUMENTS

| | | |
|---|---|---|
| EP | 0805121 B1 | 5/1997 |
| EP | 1354847 A1 | 10/2003 |
| EP | 1832548 A1 | 9/2007 |
| EP | 2234042 A1 | 9/2010 |
| FR | 2726910 A1 | 11/1994 |
| FR | 2878516 A1 | 6/2006 |
| GB | 2293658 B | 9/1995 |
| GB | 2416756 B | 11/2008 |
| JP | S59102629 A | 6/1984 |
| JP | S60252244 A | 12/1985 |
| JP | H082597 A | 6/1994 |
| JP | H107315497 A | 12/1995 |
| JP | H08128916 A | 5/1996 |
| WO | 2012/052752 A2 | 4/2012 |
| WO | 2014063823 A1 | 5/2014 |

OTHER PUBLICATIONS

Alfons Haar, PreciCONTROL—Application COP, SPDS, DTMQ, MID, FTL, "Automation in tank truck construction: Minimizes costs, weight, installation and maitenance"; [online]. Retrieved from the Internet: www.alfons-haar.de.; (2 pages).

Civacon, The Smartlok System, "The economical reliable way to strengthen the weak link in your blending process control", 1994; (4 pages).

Civacon, "Strengthen the weak link in your blending process control", 1994; (2 pages).

Civacon, The Smartlok System, "Coupling verification system by CIVACON", Jan. 1995; (9 pages).

Civacon, "Say goodbye to cross contamination: The CIVAFLO manifold system"; (4 pages).

Liquip International, Downstream News, Issue 4, Apr. 2007; (10 pages).

Measurement Specialties, "Preliminary Specification—FPS2800B12C4—Fluid Property Sensor Module", [online]. Retrieved from www.meas-spec.com; Dec. 2009; (pp. 1-5).

Sening NoMix, "Cross-Over Prevention", FMC Technologies Measurement Solutions, Inc., Apr. 2009; (4 pages).

Communication relating to the results of the Partial International Search dated Jan. 22, 2014, for International Patent Application No. PCT/US2013/069203 filed Nov. 8, 2013.

International Search Report and Written Opinion pertaining to Application No. PCT/US2013/069203 dated Nov. 8, 2013 (26 pp.).

International Preliminary Report on Patentability relating to PCT/US2013/069203 filed Nov. 8, 2013; dated May 21, 2015.

Non-Final Office Action dated Jun. 14, 2016 for U.S. Appl. No. 14/075,336, filed Nov. 8, 2013.

Final Office Action dated Oct. 11, 2016 for U.S. Appl. No. 14/075,336, filed Nov. 8, 2013.

International Search Report and Written Opinion dated Feb. 28, 2018 pertaining to Application No. PCT/US2017/056137 filed Oct. 11, 2017, 22 pages.

Invitation to Pay Additional Fees pertaining to Application No. PCT/US2017/056137 filed on Oct. 11, 2017; dated Jan. 18, 2018; 47 pages.

* cited by examiner

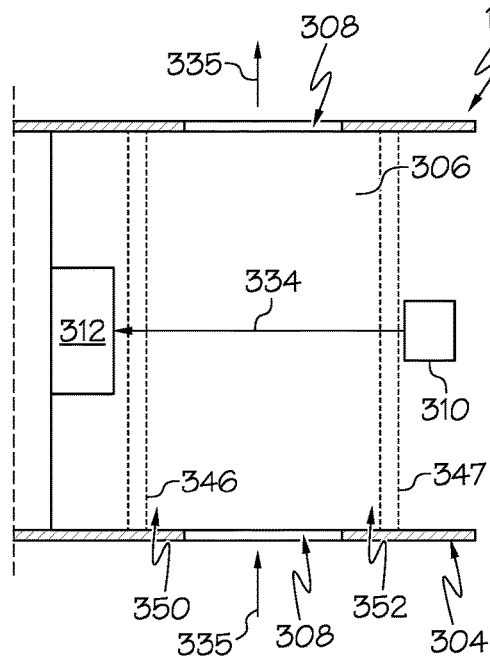
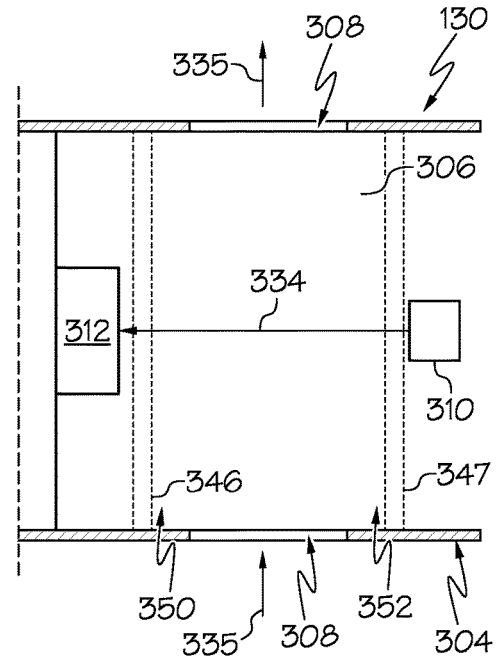
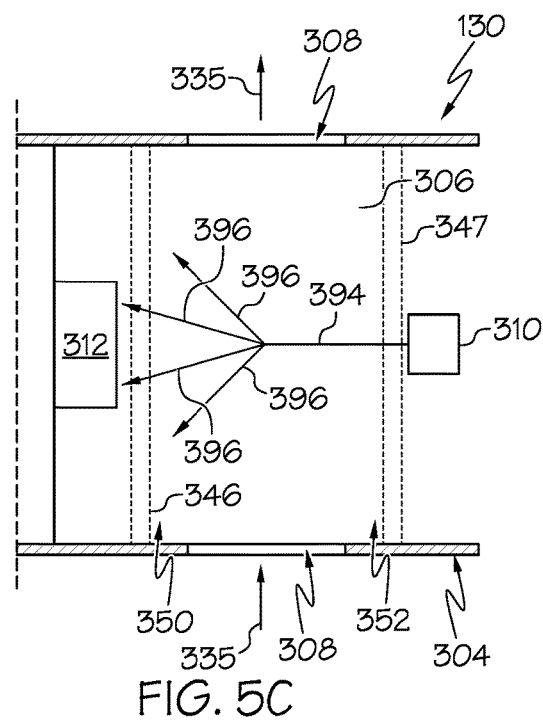

OPTICAL FLUID SENSORS FOR CROSS CONTAMINATION CONTROL SYSTEMS

FIELD

Embodiments of the present disclosure are related to optical fluid sensors, in particular optical fluid sensors for identifying fluids.

BACKGROUND

Transporting liquids, whether by tanker truck, railcar, through transfer conduits, or through other methods, involves transferring the liquid product from one vessel or tank to another vessel or tank. Conventionally, the process of transferring liquid products between vessels and/or tanks relies on an operator to ensure that two different liquids are not mixed in the tanks. Mistakenly mixing differing liquid products, such as different fuel products, can be a costly mistake. Conventional liquid property sensors utilized to help identify liquid products and avoid inadvertently mixing different liquid products are not be capable of distinguishing between certain types of liquids.

SUMMARY

Accordingly, an ongoing need exists for improved liquid property sensors for identifying the type of liquid product or fluid being transferred between storage vessels or tanks. Embodiments of the present disclosure are directed to optical fluid sensors and crossover protection systems utilizing the optical fluid sensors.

According to one or more embodiments, an optical fluid sensor may comprise a body defining a chamber and having one or more apertures to allow a fluid to enter the chamber, a light source optically coupled to the chamber and configured to emit light into the chamber, and a detector optically coupled to the chamber and configured to receive light from the chamber. The detector may measure an intensity of one or more wavelengths of light received by the detector. The light source and the detector may be positioned such that, when fluid is disposed within the chamber, emitted light from the light source passes into and through the fluid disposed in the chamber before being received by the detector.

According to one or more other embodiments, a fuel sensor may comprise a light source optically coupleable to an enclosed volume and configured to emit IR, visible, and UV spectra light and a detector optically coupleable to the enclosed volume and configured to output a signal proportional to an intensity of one or more wavelengths of IR or visible light received by the detector. The fuel sensor may further comprise a processor, one or more memory modules communicatively coupled to the processor, and machine readable instructions stored in the one or more memory modules that cause the fuel sensor to perform at least the following when executed by the processor: send a control signal to the light source to cause the light source to emit visible light into the enclosed space and emit UV light into the enclosed space, receive visible light at the detector, process the received light to determine wavelength and intensity information for the received light, and determine a fluid type of the fluid in the chamber from the wavelength and intensity information for the received light.

According to one or more embodiments, an optical sensor system may comprise a light source configured to emit UV light into a fluid, and a detector configured to measure intensities of one or more wavelengths of visible light fluoresced by the fluid in response to the UV light emitted by the light source. The optical sensor system may further comprise a processor, one or more memory modules communicatively coupled to the processor, and machine readable instructions stored in the one or more memory modules that cause the optical sensor system to perform at least the following when executed by the processor: transmit a control signal to the light source to cause the light source to emit the UV light into the fluid to cause the fluid to fluoresce, receive visible light at the detector, process the received light to determine wavelength and intensity information for the received light, compare the wavelength and intensity information for the received light to one or more fluid profiles stored in the one or more memory modules, wherein each of the one or more fluid profiles comprises information on one or more fluorescent properties of the fluid, and determine a fluid type of the fluid based on the comparison.

According to one or more other embodiments, a crossover protection system may comprise a product transport vehicle comprising a tank compartment for containing a liquid product and a valve coupled to the tank compartment, the valve regulating a flow of liquid product from the tank compartment and having a normally locked state. The crossover protection system may further comprise an optical fluid sensor positioned to contact the liquid product stored in the tank compartment. The optical fluid sensor may comprise a body defining a chamber and having one or more apertures to allow the liquid product to enter the chamber, a light source optically coupled to the chamber and configured to emit light into the chamber, and a detector optically coupled to the chamber and configured to receive light from the chamber. The detector may measure an intensity of one or more wavelengths of light received by the detector. The light source and the detector may be positioned such that, when fluid is disposed within the chamber, light passes into and through the fluid disposed within the chamber before being received by the detector. The crossover protection system may further comprise a tank delivery connector fluidly coupled to a distribution side of the valve. The tank delivery connector may comprise a tank tag reader for interrogating a tank tag coupled to a distribution tank separate from the product transport vehicle to retrieve a stored liquid type encoded on the tank tag. The stored liquid type may be indicative of a fluid type of the liquid product in the distribution tank. The crossover protection system may further comprise a system controller communicatively coupled to the valve, the optical fluid sensor, and the tank delivery connector. The system controller may comprise a processor and one or more memory modules.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 5A schematically depicts an optical fluid sensor, according to one or more embodiments shown and described herein;

FIG. 5B schematically depicts an optical fluid sensor, according to one or more embodiments shown and described herein;

FIG. 5C schematically depicts an optical fluid sensor, according to one or more embodiments shown and described herein;

DETAILED DESCRIPTION

Figure 1:
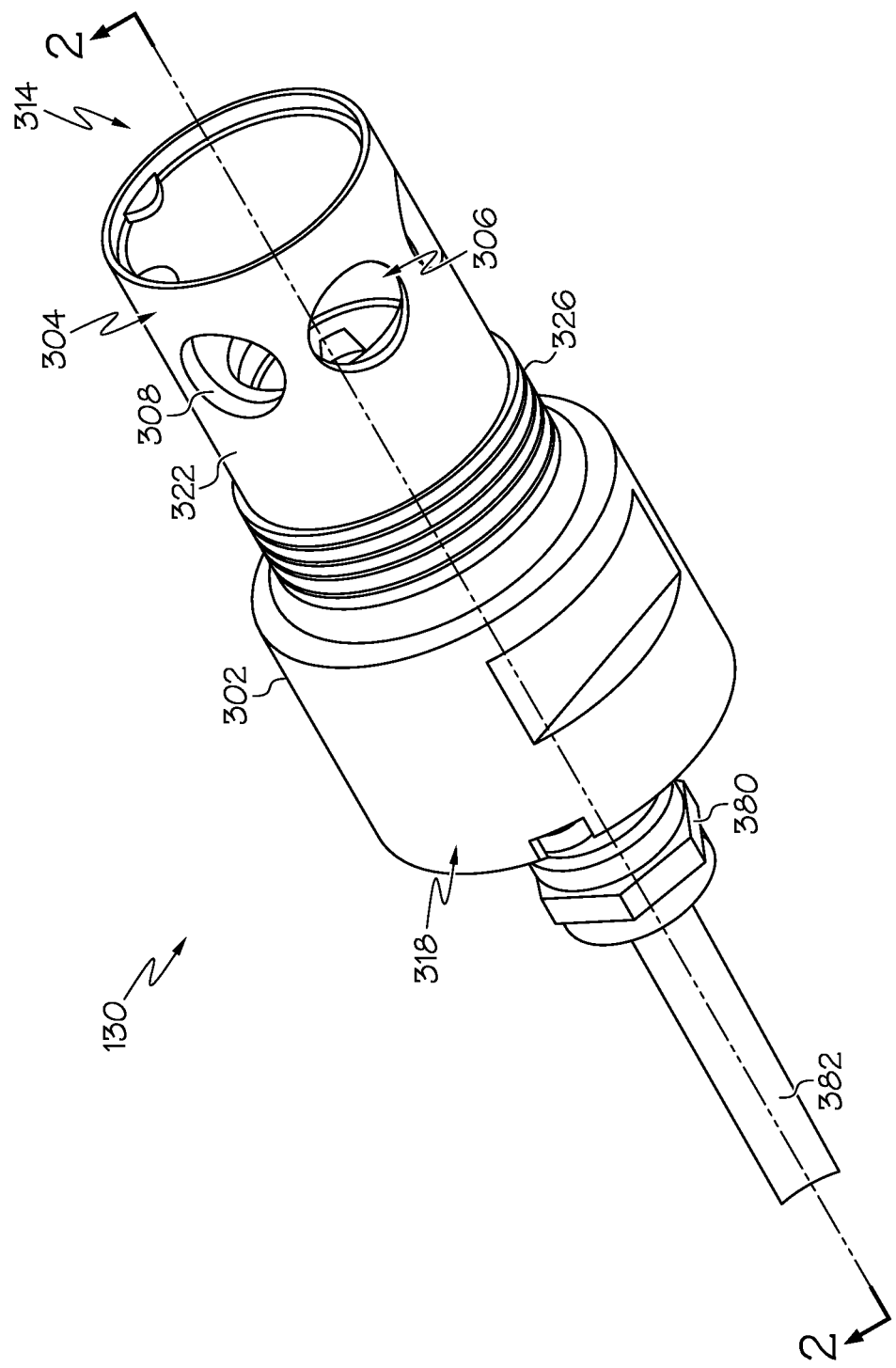
FIG. 1 is a front perspective view of an optical fluid sensor, according to one or more embodiments shown and described herein.
Figure 2:
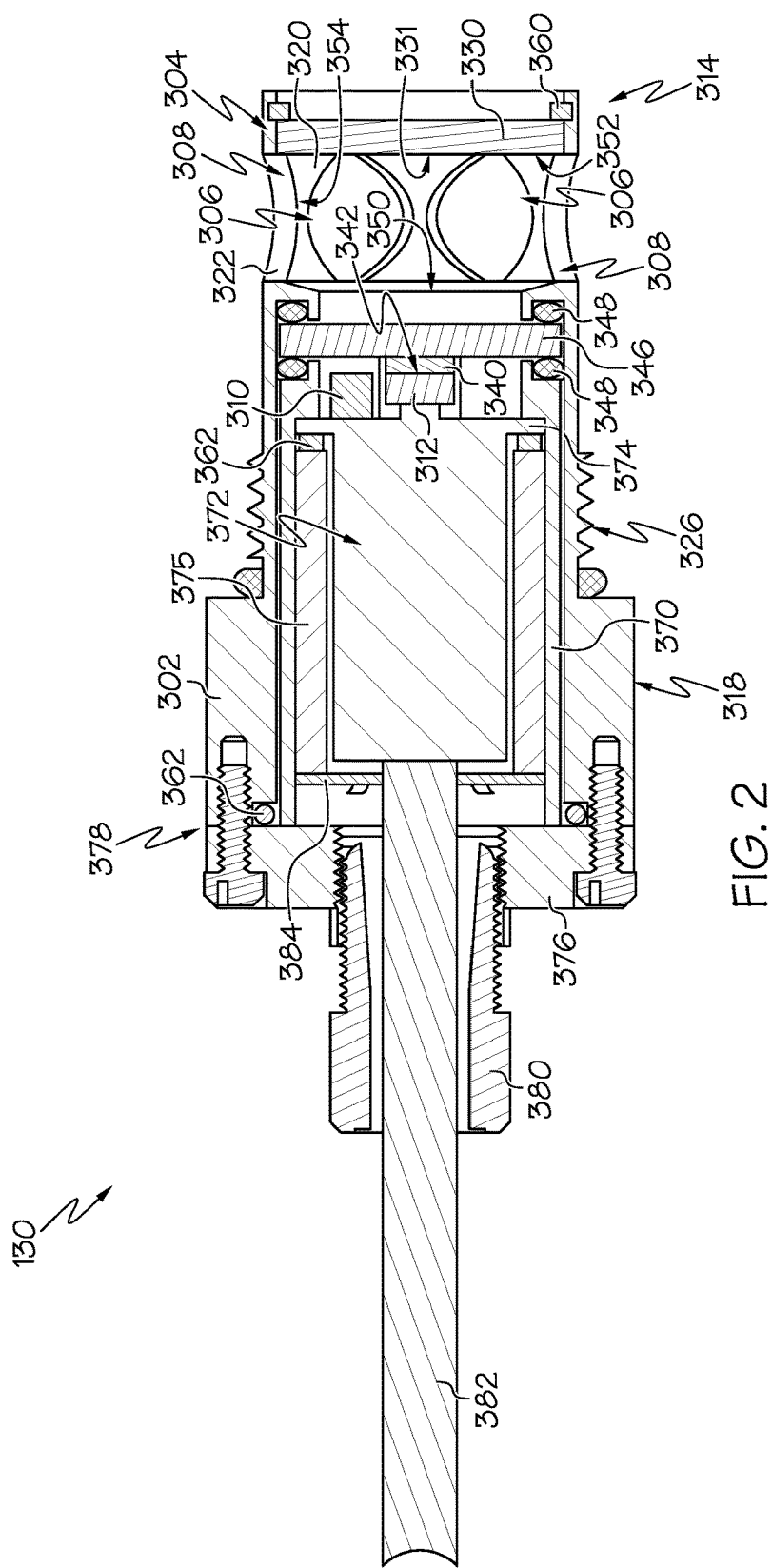
FIG. 2 is a front cross-sectional view of the optical fluid sensor of FIG. 1 taken along reference plane 2-2 in FIG. 1, according to one or more embodiments shown and described herein.

The embodiments disclosed herein include optical fluid sensors (OFS), optical sensor systems that include the OFS disclosed herein, and methods for determining a fluid type of a fluid or liquid product using the OFS and optical sensor systems disclosed herein. Crossover protection systems utilizing the OFS and optical sensor systems to prevent co-mingling and crossover contamination of dissimilar liquid products during material transfer operations are also disclosed. Referring generally to FIGS. 1 and 2, an OFS of the present disclosure may include a body that defines a chamber and one or more apertures in the chamber to allow a fluid, such as a liquid product stored in a storage tank or tank compartment, to enter the chamber. The OFS additionally may include a light source optically coupled to the chamber and configured to emit light into the chamber. The light source may be configured to emit infrared (IR) light, visible light, ultraviolet (UV) light, or combinations of these into the chamber and into the fluid disposed within the chamber. The OFS may include a detector optically coupled to the chamber and configured to receive light from the chamber. The detector may measure wavelengths and intensities of IR and visible light received by the detector. The light source and the detector may be positioned such that, when fluid is disposed within the chamber, the light emitted by the light source may pass into and through the fluid disposed in the chamber before being received by the detector. The OFS may include a processor, one or more memory modules communicatively coupled to the processor, and machine readable instructions stored in the memory modules. When executed by the processor, the machine readable instructions may cause the optical fluid sensor to transmit a control signal to the light source to cause the light source to emit IR, visible, or UV light into the chamber, receive IR or visible light at the detector, process the received light to determine wavelength and intensity information for the received light, compare the wavelength and intensity information for the received light to one or more fluid profiles stored in the memory modules, and determine a fluid type of the fluid in the chamber based on the comparison of the wavelength and intensity of the received light to the fluid profiles.

Figure 9:
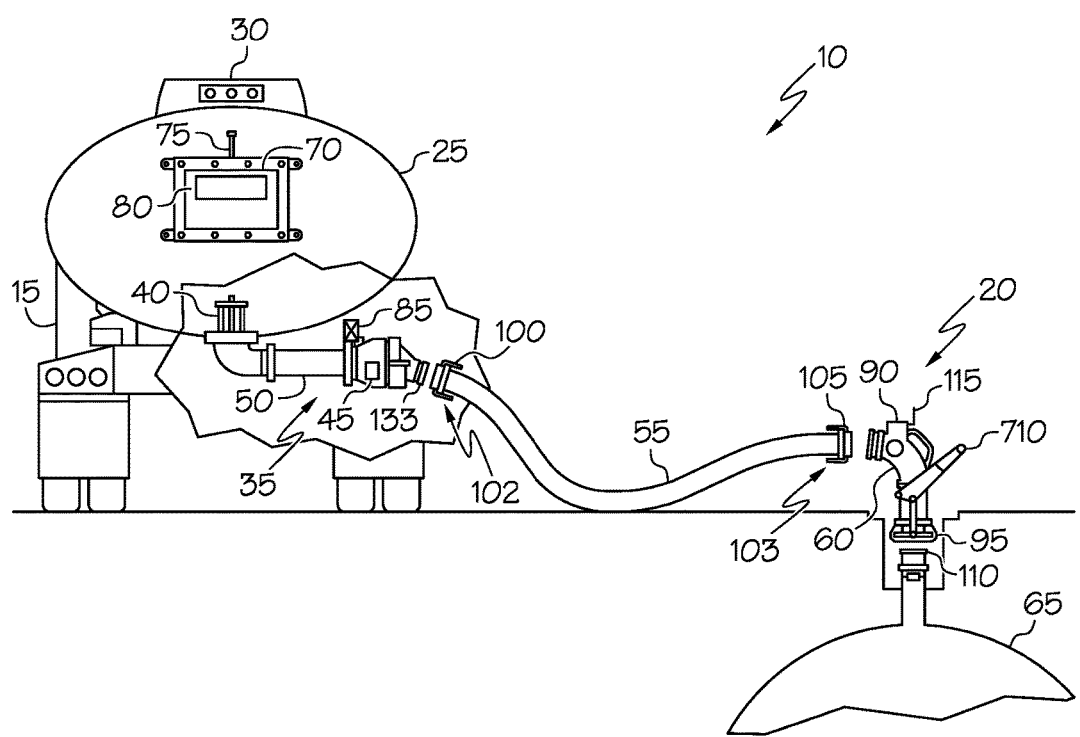
FIG. 9 schematically depicts a product transport vehicle at a product distribution station according to one or more embodiments shown and described herein.

The OFS and optical sensor systems disclosed herein may be utilized in crossover protection systems, a non-limiting example of which is generally depicted in FIG. 9, to prevent co-mingling of dissimilar liquid products when engaging in material transfer operations. The crossover protection system may be mounted on a product transport vehicle, such as a fuel truck, railcar, or other vehicle, for example. The crossover protection system may include a system controller which is communicatively coupled to at least one OFS, at least one valve, and at least one tank tag reader. For each tank compartment on the product transport vehicle there is an OFS, a valve, and, optionally, an electronic product grade indicator (PGI) controller to serve as an interface for the operator and the system controller. The PGI controller may also assist in controlling the loading and unloading of liquid product from the corresponding tank compartment. The system controller controls the flow of liquid product to and from each tank compartment through actuation of the valve. If the potential for co-mingling of dissimilar liquid products in a tank compartment and a distribution tank is present, the system controller prevents the valve corresponding to the tank compartment from being opened thus preventing the co-mingling and cross contamination of the dissimilar liquid products.

The OFS may be coupled to at least one hose adaptor assembly or tank compartment such that the OFS may detect a transported fluid type of the liquid product passing through the hose adaptor assembly or contained in the tank compartment. Accordingly, it should be understood that the OFS may be positioned to contact a liquid product (fluid) stored in the tank compartment to determine the fluid type of the liquid product stored in the tank compartment. The OFS may determine a fluid type. In embodiments, the transported fluid type, once determined, may be stored in memory and may be indexed according to the corresponding transportation tank. The OFS may transmit the fluid type in the form of a transported liquid type or an output signal indicative of the fluid type to the system controller either directly or through the PGI controller.

Referring now to FIGS. 1 and 2, the OFS 130 may include a body 302 configured to be inserted into a fuel transfer pipe (e.g., a pipe connection 50 in FIG. 9), a conduit, a storage tank (e.g., distribution tank 65 in FIG. 1), or a tank compartment 25 (FIG. 9). The body 302 may include a sensor housing 304 disposed at a sensor end 314 of the body 302. The sensor end 314 of the body 302 refers to an end of the body 302 that is inserted into the transfer pipe, conduit, storage tank, or tank compartment 25 (FIG. 9) and generally contacts the fluid in the transfer pipe, conduit, storage tank, or tank compartment 25. The sensor housing 304 may define a chamber 306 and may define one or more apertures 308 extending through the sensor housing 304 to enable fluid to flow into the chamber 306. As used herein, the term "chamber" may refer to a fully or partially enclosed volume. The apertures 308 may be disposed in any side of the housing 304 or in an end of the housing 304. In one or more embodiment, the chamber 308 may be an open-sided recess or pocket in an end of the housing 304 such that the chamber 308 is only partially enclosed by the housing 304 and open to the fluid.

Referring to FIG. 2, the OFS 130 may include a light source 310 optically coupled to the chamber 306 and configured to emit light into the chamber 306 and a detector 312 optically coupled to the chamber 306 and configured to receive light from the chamber 306. The light source 310 may be capable of producing light in the infrared (IR), visible, and ultraviolet (UV) spectra. The detector 312 may be capable of measuring the intensities and wavelengths of IR and visible light received by the detector 312. The OFS 130 may include an OFS controller 402 (FIG. 6) that receives a signal from the detector 312 indicative of the wavelengths and intensities of light received by the detector 312, processes the signal information from the detector 312 to determine the wavelength and intensity information of the light received at the detector 312 (i.e., the received light), compares the wavelength and intensity information for the received light to one or more fluid profiles, and determines a fluid type of the fluid disposed within the chamber 306 based on the comparison of the wavelength and intensity information of the received light to the one or more fluid profiles.

Figure 3:
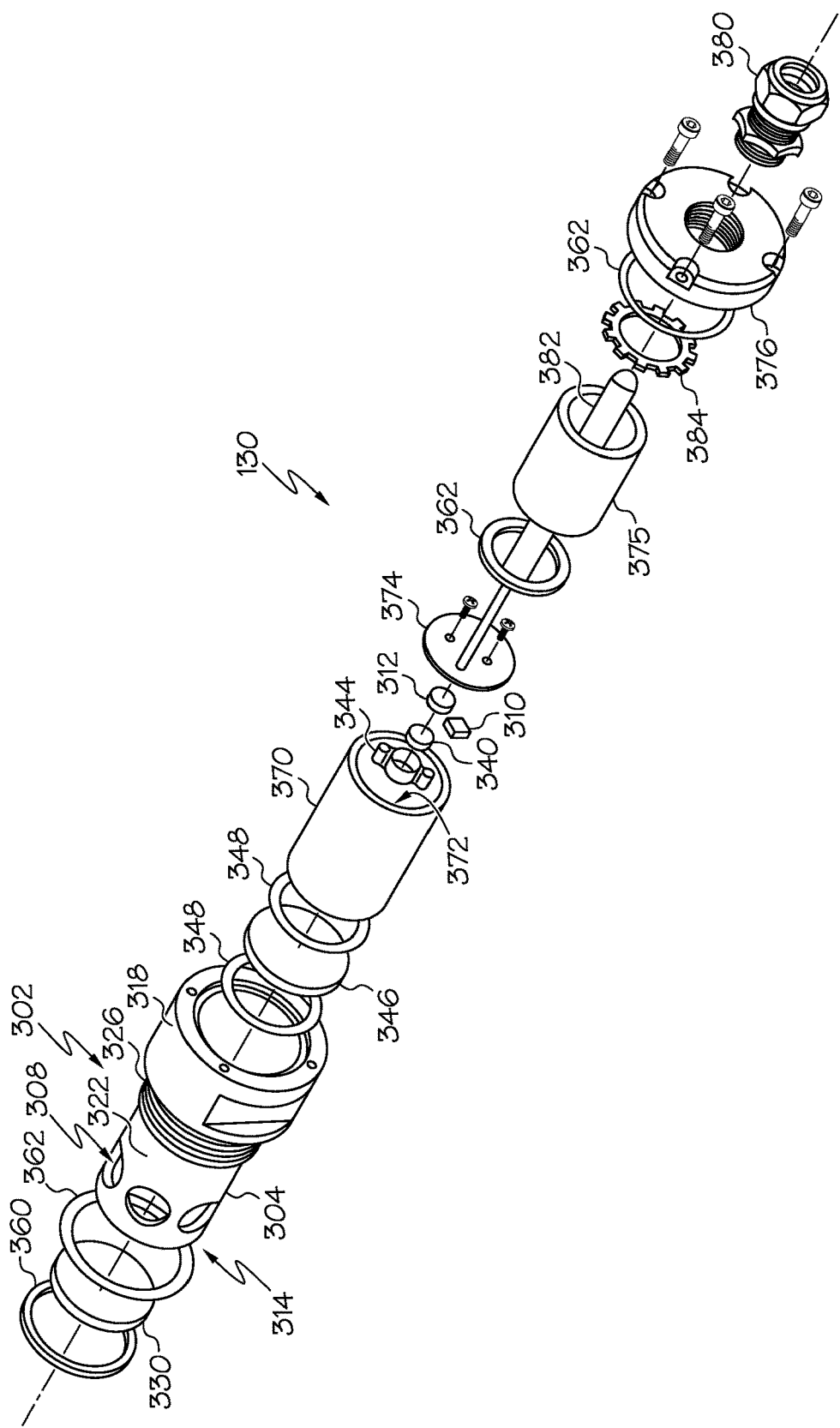
FIG. 3 is an exploded perspective view of the optical fluid sensor of FIG. 1, according to one or more embodiments shown and described herein.

Referring to FIGS. 1-3, the body 302 of the OFS 130 may include an electronics portion 318 coupled to or integral with the sensor housing 304. The electronics portion 318 of the body 302 may be generally positioned at an end of the body opposite the sensor end 314 and may be generally disposed external to the transfer pipe, conduit, storage tank, or tank compartment to which the OFS 130 is installed. The electronics portion 318 of the body 302 may not be in contact with the fluid. As previously discussed, the sensor housing 304 defines the chamber 306 and the one or more apertures 308 that enable fluid to flow into and/or out of the chamber 306. In one or more embodiments, the chamber 306 may be defined internally within the sensor housing 304 such that the chamber 306 is defined by an inner side 320 (FIG. 2) of an outer wall 322 of the sensor housing 304. In one or more embodiments, the sensor housing 304 may be cylindrical in shape and the apertures 308 may be disposed in the outer walls 322 of the sensor housing 304. The sensor housing 304 may have any other convenient shape.

Figure 16:
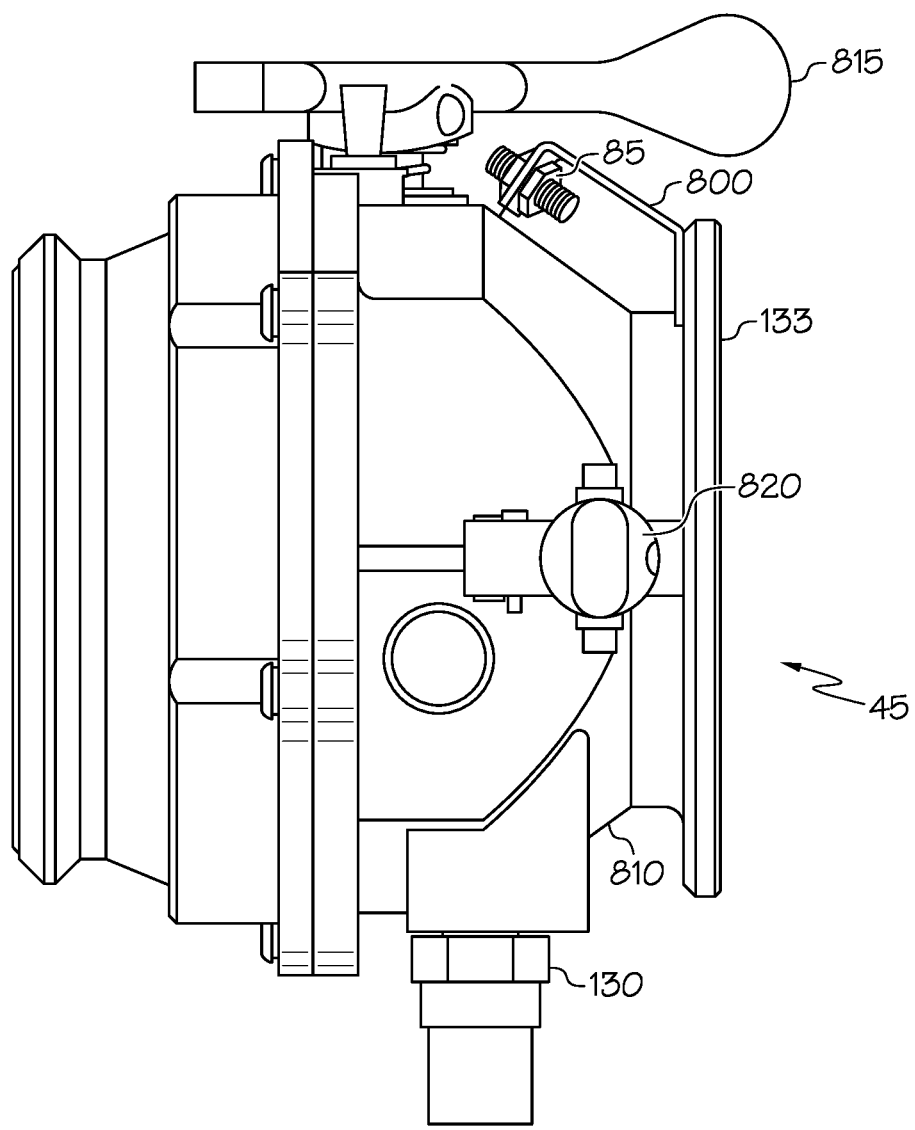
FIG. 16 is a side view of the control valve according to one or more embodiments shown and described herein.

The body 302 may be configured to couple the OFS 130 to a fitting, such as the hose adaptor assembly 35 (FIG. 9), for inserting the sensor housing 304 of the OFS 130 into a fuel transfer pipe, conduit, storage tank, or tank compartment. In one or more embodiments, the body 302 may include a threaded portion 326 for removeably attaching the body 302 into the fitting. Although a threaded portion 326 is described herein, it is contemplated that one or more other coupling means, such as clips, welds, or sockets for example, may be utilized for coupling the body 302 of the OFS 130 to the fitting. In one or more embodiments, the body 302 may be configured to interface and removeably couple with a control valve 45 (FIGS. 9 and 16). A non-limiting example of a suitable control valve 45 is the API Adaptor, model number 891BA-LK by Civacon. In one or more embodiments, the body 302 may be removeably coupleable to a port (not shown) positioned in a tank compartment 25 (FIG. 9). The body 302 of the OFS 130 may be configured to isolate the detector 312 from ambient sources of light so that the detector 312 is exposed only to light emitted by the light source 310 into the chamber 306 or visible light fluoresced by the fluid in the chamber 306 in response to UV light emitted by the light source 310.

The body 302 may be constructed of a material compatible with the fluids and liquid products with which the OFS 130 may come into contact. In one or more embodiments, the body 302 may be corrosion resistant and chemically resistant. In one or more embodiments, the body 302 may be chemically resistant to organic solvents and/or petroleum-based fuel compositions.

The light source 310 may be capable of producing IR spectrum light, visible spectrum light, UV spectrum light, or combinations of IR, visible, and UV spectra light. In one or more embodiments, the light source 310 may emit IR light, visible light, and UV light. The light source 310 may be one or more light emitting diodes (LED). Although embodiments comprising LEDs are described subsequently in this disclosure, it is contemplated that other types of light emitting devices may be used in the light source 310 to produce the light. Non-limiting examples of light emitting devices that may be used for the light source 310 may include, but are not limited to, incandescent light bulbs, fluorescent lamps, metal-halide lamps, halogen lamps, lasers, neon lamps, argon lamps, or other light emitting devices. LEDs may include, but are not limited to, organic LEDs, polymer LEDs, active matrix organic LEDs, other LEDs, or combinations thereof.

The light source 310 may be a single light emitting device capable of producing the different types of light under different operating conditions, or the light source 310 may include a plurality of light emitting devices, at least one light emitting device configured to emit at least one of IR light, visible light, or UV light. In one or more embodiments, the light source 310 may be a single LED and the operating conditions, such as power input or use of one or more lens filters for example, may be manipulated to produce IR light, visible light, UV light, or combinations of these. In one or more embodiments, the light source 310 may comprise a plurality of LEDs, at least one of which may be configured to produce IR light, at least one of which may be configured to produce visible light, and at least one of which may be configured to produce UV light. In one or more embodiments, the light source 310 may include at least one LED producing white light. In one or more embodiments, the light source 310 may include at least one LED producing visible light in the red visible spectrum, at least one LED producing visible light in the green visible spectrum, and at least one LED producing light in the blue visible spectrum. In one or more embodiments, the light source 310 may comprise multiple LEDs for producing the visible light, and each of the multiple LEDs may produce one or more of red, orange, yellow, green, blue, or violet spectra of visible light. In one or more embodiments, the light source 310 may include six or more LEDs for producing the visible light with at least one LED for each of the red, orange, yellow, green, blue, and violet wavelength ranges (spectra) of visible light.

The detector 312 may include any device capable of receiving the light and detecting the wavelength and intensity of light. The detector 312 may be capable of detecting the wavelength and intensity of IR light, visible light, or both IR and visible light. The detector 312 may be capable of detecting the wavelength and intensity of other spectra of light. In one or more embodiments, the detector 312 may be capable of detecting the wavelength and intensity of both IR light and visible light received by the detector 312. The detector 312 may be configured to measure the intensity of wavelengths of light received by the detector 312. The detector 312 may be one or more photo diodes, imaging systems, or combinations of these. Although embodiments that include photo diodes are described in further detail in this disclosure, it is contemplated that other types of detectors or detection systems capable of measuring wavelengths and intensities of IR or visible light may be used in the OFS 130. In one or more embodiments, the detector 312 may be adapted to receive and measure wavelengths and intensities of visible light fluoresced by the fluid in response to UV light emitted by the light source 310. In one or more embodiments, the detector 312 may be configured to output a signal proportional to an intensity of one or more wavelengths of IR or visible light received at the detector 312. The output signal of the detector 312 may be indicative of the wavelength and intensity of the IR or visible light received at the detector 312.

The detector 312 may include a single detector capable of detecting IR and visible spectrum light. The detector 312 may additionally include multiple detectors, each detector 312 capable of detecting wavelengths within specific wavelength ranges of IR or visible light. In one or more embodiments, the detector 312 may have an IR portion for detecting IR light and a visible portion for detecting visible light. The detector 312 may be configured to simultaneously detect the wavelengths and intensities of IR light and the wavelengths and intensities of visible light. In one or more embodiments, the detector 312 may include a plurality of photo diodes, at least one photo diode for detecting IR light and at least one photo diode for detecting visible light. In one or more embodiments, the detector 312 may include a single photo diode, and one or more optical and/or mathematical filters may be used to enable the single photo diode to measure the wavelengths and intensities for both IR and visible light. In one or more embodiments, the detector 312 may include one photo diode for detecting IR light and a plurality of photo diodes for detecting visible light. Each of the visible light photo diodes may correspond to a specific range of wavelengths of visible light. In one or more embodiments, the detector 312 may have at least three photo diodes for detecting visible light: at least one red spectrum diode for detecting red wavelengths of visible light, at least one green spectrum diode for detecting green wavelengths of visible light, and at least one blue spectrum diode for detecting blue wavelengths of visible light. In one or more embodiments, the detector 312 may have at least six photo diodes, one photo diode for each of red, orange, yellow, green, blue, and violet spectra ranges of visible light. In one or more embodiments, the detector 312 may be an imaging system adapted to measure the wavelengths and intensity of IR and/or visible light.

Various combinations of light sources, detectors, and/or filters may be utilized to focus the OFS 130 on one or more specific wavelength ranges of light. In one or more embodiments, the light source 310 may be a single white light, and the detector 312 may include a plurality of detecting elements, such as a plurality of photo diodes, each of which is configured to measure the intensity of light in a specific wavelength range. In one or more embodiments, the light source 310 may be a single white light, and one or more optical filters may be utilized and interchanged to filter the light returning to the detector so that only certain wavelengths of light are received by the detector. In one or more embodiments, the light source 310 may be a single white light, and one or more mathematical filters may be utilized by the OFS controller 402 (FIG. 6) to filter the signal received from the detector 312 to receive data only for the one or more specific wavelength ranges. In one or more embodiments, the light source 310 may include a plurality of light emitting devices, each capable of emitting light in a specific wavelength range, and the detector 312 may be a single detector to detect the specific wavelength ranges of light emitted by the plurality of light emitting devices of the light source 310.

Referring to FIGS. 2 and 3, the detector 312 may include a UV filter 340 to protect the detector 312 from exposure to UV light from the light source 310. For a detector 312 having photo diodes, the detector 312 may be sensitive to UV light. As explained subsequently in this disclosure, the OFS 130 may measure the visible light fluoresced by the fluid in the chamber 306. When operating to measure the wavelengths and intensities of visible light fluoresced by the fluid, the detector 312 may be simultaneously exposed to UV light emitted by the light source 310 and visible light fluoresced by the fluid in the chamber 306 in response to the UV light. The UV filter 340 may be used to prevent exposure of the detector 312 to the UV light while simultaneously allowing the visible light to penetrate and irradiate the detector 312 for measurement of the wavelengths and intensities of visible light fluoresced by the fluid. The UV filter 340 may be a coating or film applied directly to a surface 342 (FIG. 2) of the detector 312 or may be a separate UV filter lens positioned between the detector 312 and the chamber 306 such that optical communication between the chamber 306 and the detector 312 passes through the UV filter lens. In one or more embodiments, the OFS 130 may include a filter lens housing 344 (FIG. 3) disposed around the UV filter 340. The filter lens housing 344 may prevent UV light from bypassing or going around the UV filter 340 to reach the detector 312.

Both the light source 310 and the detector 312 may be optically coupled to the chamber 306 defined in the sensor housing 304 such that the light source 310 and the detector 312 are in optical communication with the fluid disposed within the chamber 306. The light source 310 may be optically coupled with the chamber 306 so that, when the fluid is disposed within the chamber 306, the light emitted by the light source 310 passes into the chamber 306 and through the fluid disposed within the chamber 306. The detector 312 may be optically coupled to the chamber 306 so that, when fluid is disposed within the chamber 306, the detector 312 may receive light passing through the fluid in the chamber 306 or visible light fluoresced by the fluid in the chamber 306 in response to the UV light emitted by the light source 310. In one or more embodiments, the light source 310, the detector 312, or both may be disposed within the chamber 306 and may be in direct contact with the fluid disposed within the chamber 306. Referring to FIGS. 2 and 3, in one or more embodiments, the light source 310, detector 312, or both may be fluidly isolated from the fluid in the chamber 306 by a transparent member. The transparent member may allow light from the light source 310 to pass through into the fluid, but may prevent the fluid from contacting the light source 310 and/or the detector 312. The transparent member may be one or more windows 346. The window 346 may be plastic, glass, or other material that is generally transparent to at least IR, visible, and UV light. In one or more embodiments, the window 346 may not substantially impede the light traveling through the window 346, which impedence may influence the wavelengths and intensities of the light received and measured by the detector 312. In one or more other embodiments, the OFS controller 402 (FIG. 6) may include one or more algorithms for correcting the wavelength and intensity information for the light received by the detector 312 for any effects caused by the light passing throughout the window 346. In one or more embodiments, the window 346 may be Pyrex® brand glass by Corning Incorporated. The window 346 may allow IR, visible, and UV light to pass through the window 346 such that the light source 310 and the detector 312 remain in optical communication with the chamber 306 while at the same time being fluidly isolated from the fluid in the chamber 306. One or more sealing members 348 may be disposed between the window 346 and the body 302 of the OFS 130 to maintain a fluid tight seal to fluidly isolate the light source 310 and detector 312 from the fluid in the chamber 306.

Figure 4A:
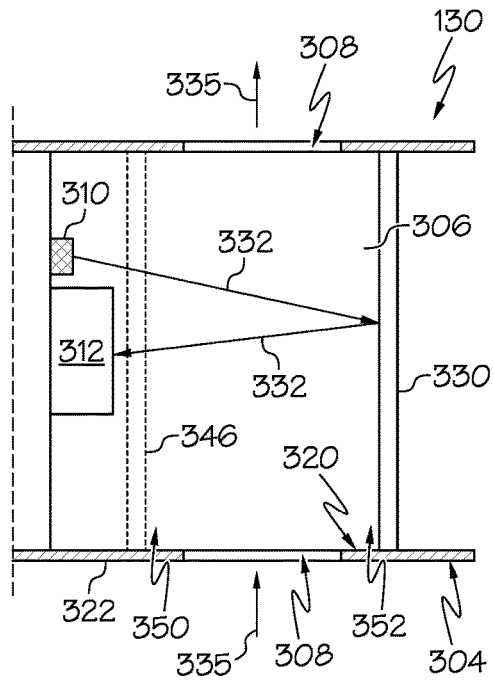
FIG. 4A schematically depicts an optical fluid sensor, according to one or more embodiments shown and described herein.
Figure 4B:
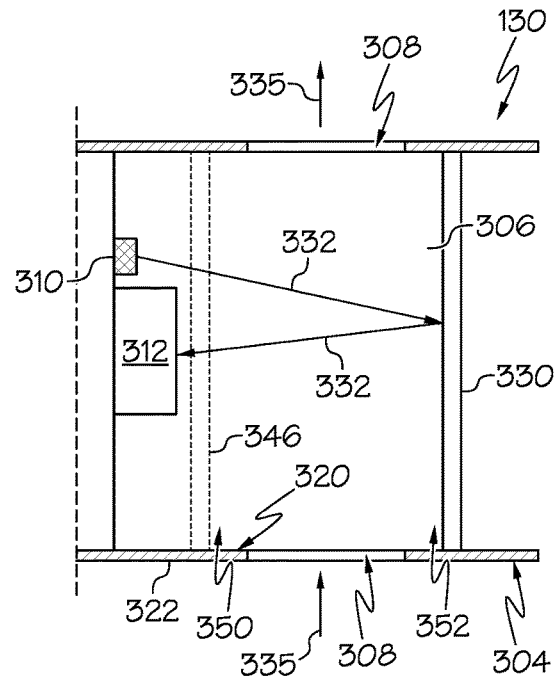
FIG. 4B schematically depicts an optical fluid sensor, according to one or more embodiments shown and described herein.
Figure 4C:
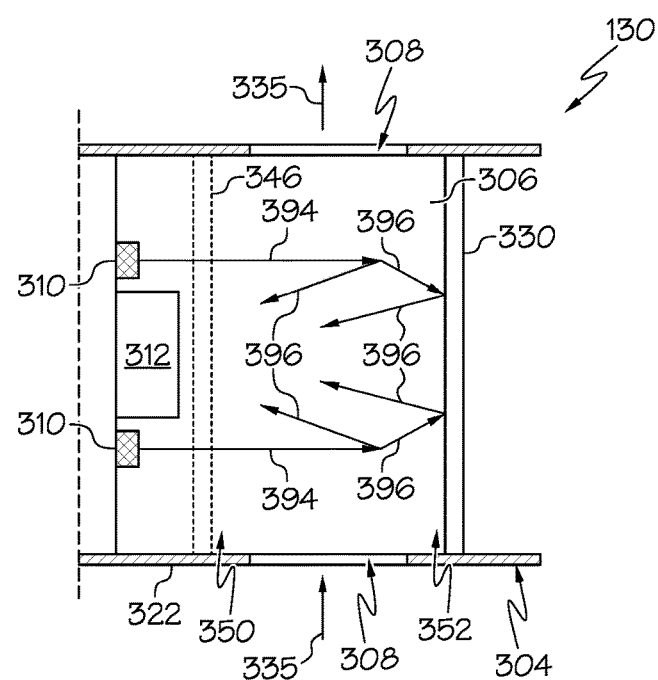
FIG. 4C schematically depicts an optical fluid sensor, according to one or more embodiments shown and described herein.

Referring to FIGS. 4A-4C, the light source 310 and the detector 312 may be positioned at or adjacent to a first side 350 of the chamber 306 such that both the light source 310 and the detector 312 are optically coupled to the chamber 306 from the same side of the chamber 306. A reflector 330 may be positioned at or adjacent to a second side 352 of the chamber 306 opposite from the light source 310 and the detector 312. The reflector 330 may be positioned so that the reflector 330 reflects the light emitted into the chamber 306 by the light source 310 towards the detector 312. The arrows 335 in FIGS. 4A-4C denote the flow of fluid through apertures 308 into and out of the chamber 306. As shown in FIGS. 4A and 4B, which illustrate the light source 310 and detector 312 positioned at the same side (first side 350) of the chamber 306, when fluid is disposed within the chamber 306, at least a portion of the light (e.g., visible or IR) emitted from the light source 310 passes into the chamber 306, travels through the fluid disposed in the chamber 306, reflects off of the reflector 330, travels back through the fluid in the chamber 306 to the detector 312, where the emitted light is received by the detector 312.

An optical communication pathway 332 may be defined as a path of travel of the light from the light source 310, through the fluid disposed within the chamber 306, and to the reflector 330, and then from the reflector 330, back through the fluid in the chamber 306, and to the detector 312. When the fluid is disposed within the chamber 306, the IR and visible light may pass into and through the fluid in the chamber 306 when traveling along the optical communication pathway 332 from the light source 310 to the detector 312. In one or more embodiments, the first side 350 of the chamber 306, at or adjacent to which the light source 310 and detector 312 are disposed, may be positioned closer to the electronics portion 318 of the body 302 and may be oriented to face generally toward the sensor end 314 of the body 302, and the second side 352 of the chamber 306 may be positioned between the sensor end 314 of the body 302 and the chamber 306 and may face generally towards the first side 350 of the chamber 306 (i.e., towards the electronics portion 318 of the body 302). In one or more embodiments, the light source 310 and detector 312 may be on the same side (i.e., the first side 350) of the chamber 306, and the chamber 306 may be an open-sided chamber without a second side 352 (i.e., without a reflector) so that the light is emitted from the light source 310 into the fluid and the detector 312 detects light reflected by the fluid.

Referring to FIGS. 5A and 5B, in one or more embodiments, the light source 310 may be positioned at or adjacent to the second side 352 of the chamber 306, and the detector 312 may be positioned at or adjacent to the first side 350 of the chamber 306 such that the detector 312 and the light source 310 are positioned facing one another. The second side 352 of the chamber 306, at or adjacent to which the light source 310 is positioned, may be directly opposite the first side 350 of the chamber 306 such that, when the fluid is disposed within the chamber 306, light emitted from the light source 310 travels along a generally linear path 334 from the light source 310, through the fluid in the chamber 306, and to the detector 312. A supplemental window 347 may be positioned between the light source 310 and the chamber 306 to fluidly isolate the light source 310 from the fluid in the chamber 306. The arrows 335 in FIGS. 5A-5C denote the flow of fluid through apertures 308 into and out of the chamber 306. With the light source 310 positioned at the second side 352 opposite the detector 312 and the fluid disposed within the chamber 306, light emitted by the light source may travel along a generally linear path 334 from the light source 310, through the fluid, and to the detector 312. In one or more embodiments, the detector 312 may be positioned at or adjacent to the second side 352 of the chamber 306, and the light source 310 may be positioned at or adjacent to the first side 350 of the chamber 306. In one or more embodiments, the light source 310 or the detector 312 may be positioned at or adjacent to a third side 354 of the chamber 306, which may be oriented at an angle relative to the first side 350, and one or more reflectors 330 may be positioned within or in optical communication with the chamber 306 to reflect IR and/or visible light from the light source 310 to the detector 312. In one or more embodiments, a plurality of reflectors 330 may be positioned within or in optical communication with the chamber 306 to redirect light emitted from the light source 310 to the detector 312.

Referring back to FIG. 2, the reflector 330 may be optically coupled to the chamber 306 so that light from the light source 310 or visible light fluoresced by the fluid in response to UV light from the light source 310 may contact and be reflected from a reflective surface 331 of the reflector 330. The reflector 330 may be positioned within the chamber 306 and in contact with the fluid disposed within the chamber 306. In one or more embodiments, the reflector 330 may include a chemical and/or solvent resistant material in contact with the fluid in the chamber 306. In one embodiment, the reflector 330 may have a reflective surface 331 that may be a polytetrafluoroethylene, such as Teflon™, which is produced and marketed by The Chemours™ Company. Alternatively, the reflector 330 may be fluidly isolated from the chamber 306 by a reflector window (not shown). The reflector window may allow light to pass through to maintain optical communications between the reflector 330 and the chamber 306 while simultaneously fluidly isolating the reflector 330 from the fluid disposed within the chamber 306. The reflector 330 may be removably coupled to the sensor end 314 of the body 302 by a snap ring 360, end cap (not shown), or other coupling means. A sealing member 362, such as a gasket or o-ring, may be disposed between the reflector 330 and the sensor housing 304.

Referring to FIGS. 2 and 3, the OFS 130 may include an electronics holder 370 positioned within the electronics portion 318 of the body 302. The electronics holder 370 may define an electronics compartment 372, which may be a generally cylindrical hollow cavity, within the electronics holder 370. One or more electronic components, such as a circuit board 374 (FIG. 3), the light source 310 (FIG. 2), the detector 312 (FIG. 2), other electronic component, or combinations of these, for example, may be disposed within the electronics compartment 372 in the electronics holder 370. The electronics compartment 372 may be fluidly isolated from the chamber 306 in the sensor housing 304 such that fluid from the chamber 306 does not contact the electronic components contained within the electronics compartment 372. In one or more embodiments, the electronics compartment 372 may be fluidly isolated from the chamber 306 by the window 346 and the sealing members 348. In one or more embodiments, the electronics holder 370 may include a spacer 375 (FIG. 3) to position the one or more electronic components within the electronics compartment 372.

Referring to FIGS. 2 and 3, an end cap 376 may be removeably coupled to an end 378 of the body 302, the end 378 being generally opposite from the sensor end 314 of the body 302. The end cap 376 may maintain the electronics holder 370 and electrical components within the body 302 of the OFS 130. The end cap 376 may have an electrical fitting 380 for passing one or more electrical cables 382 through the end cap 376 to the electrical components. The electrical cables 382 may include a power supply cable and one or more electronic communication cables. The OFS 130 may include one or more seal members 362 to maintain a fluid-tight seal around the electronics holder 370 to fluidly isolate the electronics compartment 372 from fluid intrusion. The OFS 130 may also include a retaining ring 384 disposed between the end cap 376 and the electronics holder 370.

Figure 6:
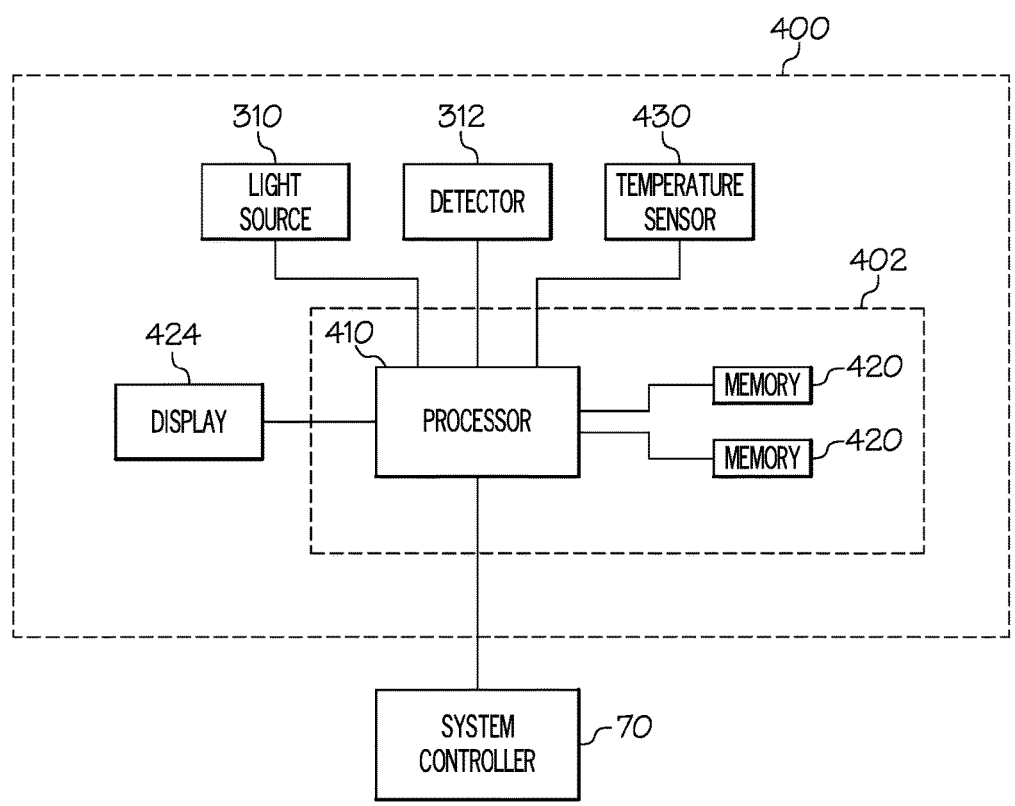
FIG. 6 schematically depicts an optical sensor system with an optical fuel sensor, according to one or more embodiments shown and described herein.

Referring now to FIG. 6, an optical sensor system 400 may include the light source 310 and detector 312 of the OFS 130 and an OFS controller 402, which may include at least one processor 410 and at least one memory module 420 communicatively coupled to the processor 410. In one or more embodiments, the OFS controller 402, including the processor 410 and memory module 420, may be disposed on the circuit board 374 (FIG. 3) positioned within the electronics holder 370 (FIG. 3). The OFS controller 402 may be communicatively coupled with the light source 310 to provide a control signal to the light source 310. The OFS controller 402 may be communicatively coupled with the detector 312 to receive the wavelength and intensity information or an output signal indicative of the wavelength and intensity of received light from the detector 312. The OFS controller 402 may also be communicatively coupled with a system controller 70 (FIG. 10) and may receive control signals from and transmit information to the system controller 70. Communication between the OFS controller 402 and/or the OFS 130 itself and the system controller 70 (FIG. 10) may be through one or more wired, wireless, or optical communication. The optical sensor system 400 may optionally include an OFS display 424, which may be communicatively coupled to the OFS controller 402. In one or more embodiments, the OFS display 424 may be positioned externally relative to the body 302 of the OFS 130 and may be communicatively coupled to the OFS controller 402 by one or more of the electrical cables 382 (FIG. 3).

The optical sensor system 400 may also include one or more temperature sensors 430. The temperature sensors 430 may be positioned in the electronics holder 370 (FIG. 3) to measure a temperature of the electronic components or may be positioned in the chamber 306 to measure a fluid temperature. In one or more embodiments, at least one of the temperature sensors 430 may be coupled to the circuit board 374 of the OFS 130 so that the temperature sensor 430 measures the temperature of the electronic components, which may include one or more of the light source 310, detector 312, OFS controller 402, processor 410, memory modules 420, other electronic components, or combinations of these. In one or more embodiments, the temperature sensor 430 may be a piezoelectric temperature sensor. In one or more embodiments, the temperature sensor 430 may be a chip coupled to the circuit board 374. In one or more embodiments, one of the temperature sensors 430 may be positioned within the chamber 306 to measure the fluid temperature when the fluid is disposed within the chamber. In one or more embodiments, the OFS 130 may have at least one temperature sensor 430 positioned within the electronics holder 370 to measure a temperature of the electronics and at least one temperature sensor (not shown) positioned within the chamber 306 of the sensor housing 304 to measure the fluid temperature. Each of the one or more temperature sensors 430 may be communicatively coupled with the OFS controller 402 for communicating temperature information to the OFS controller 402.

The one or more memory modules 420 may have one or more fluid profiles for one or more fluids (e.g., liquid products) stored therein. The fluid profiles may be in the form of one or more look-up tables (LUT). The fluid profiles stored in the memory modules 420 may be indexed by fluid type. Each fluid profile may include a transmissivity profile for a specific fluid. The transmissivity profile may include information on the wavelengths and intensities of visible light transmitted through the fluid or reflected by the fluid. In one or more embodiments, each fluid profile may include a plurality of transmissivity profiles for the fluid, with each transmissivity profile providing transmissivity information for a specific temperature of the light source 310, fluid temperature, or both. In addition or in the alternative, each fluid profile may include a light absorption profile for the fluid, the absorption profile including information on the wavelengths and intensities of light absorbed by the fluid. Each fluid profile may also include a fluorescence profile, which may include information on the wavelengths and intensities of visible light fluoresced by the fluid in response to UV light. In one or more embodiments, each fluid profile may include a plurality of fluorescence profiles for the fluid, each fluorescence profile including fluorescence information for a specific temperature of the light source 310, fluid temperature, or both. In one or more embodiments, the fluid profile may include a color of the fluid. The color of the fluid may be expressed as the wavelengths and intensities of visible light reflected by the fluid when exposed to visible light. In one or more embodiments, the memory modules 420 may include fluid profiles for specific liquid products that are expected to be encountered by the OFS 130. In one or more embodiments, the memory module 420 may include a temperature algorithm for adjusting data received from the detector 312 to account for changes in the temperature of the electronics, fluid temperature, or both. The memory modules 420 may also have machine readable instructions stored thereon that, when executed by the processor 410, cause the OFS controller 402 to operate the OFS 130 to determine a fluid type of the fluid in the chamber 306 or to determine whether a fluid is in the chamber 306.

Referring back to FIGS. 4A-4C, the OFS 130 may be used to determine whether a fluid is present in the chamber 306 and to determine a fluid type of the fluid in the chamber 306 based on the visible light transmitted through the fluid, the visible light fluoresced by the fluid in response to UV light, or both. The OFS 130 may be utilized to determine the fluid type for many different liquid products, such as petroleum-based fuels (e.g., diesel fuel, gasoline, kerosene), organic solvents, oils, resins, aqueous solutions, other fluids, or combinations of fluids. In one or more embodiments, the fluid may be a liquid product that is a petroleum-based fuel, and the OFS 130 may be used to determine a type of petroleum-based fuel, which may include diesel fuels, fuels with differing octane numbers, fuels having varying concentrations of one or more alcohols, fuels containing one or more dyes, or other fuels. In one or more embodiments, the fluid may be a vapor or gas, such as fuel gas or natural gas, for example.

Referring to FIGS. 4A and 5A, the OFS 130 may use IR light to determine whether a fluid is present in the chamber 306 of the sensor housing 304. FIG. 4A schematically depicts an embodiment of the OFS 130 in which the light source 310 and the detector 312 are positioned on or adjacent to the same side (first side 350) of the chamber 306 with the reflector 330 positioned on the opposite side (second side 352) of the chamber 306. The OFS controller 402 (FIG. 6) may send a signal to the light source 310 to cause the light source 310 to emit IR light into the chamber 306, which then may cause the light source 310 to emit the IR light into the chamber 306. The IR light may be emitted by an IR portion of the light source 310. The IR light travels along an optical communication pathway 332, along which the IR light travels through the chamber 306, reflects off of the reflector 330 positioned on the opposite side (second side 352) of the chamber 306, travels back through the chamber 306, and is received by the detector 312, which measures the intensity of the IR light received. The intensity of the IR light may be measured by an IR portion of the detector 312. FIG. 5A illustrates an embodiment in which the light source 310 is positioned on an opposite side (second side 352) of the chamber 306 from the detector 312. In this embodiment, the IR light emitted by the light source 310 travels along a generally linear path 334 through the fluid in the chamber 306 and to the detector 312.

Certain fluids, such as petroleum-based fuels for example, absorb IR light. When a fluid is present in the chamber 306, the fluid may absorb some of the IR light traveling through the fluid. The remaining IR light passes through the fluid and reaches the detector 312. Because some of the IR light is absorbed, less IR light reaches the detector 312 compared to the intensity of the IR light emitted by the light source 310. When a fluid is present in the chamber 306, the intensity of the IR light received by the detector 312 may be substantially less than the IR light emitted by the light source 310 into the chamber 306. Therefore, a substantial decrease in the intensity of the IR light from the light source 310 to the detector 312 may indicate that fluid is disposed within the chamber 306. The memory modules 420 (FIG. 6) may include one or more IR threshold intensities, which are less than the intensity of the IR light emitted by the light source 310. In one or more embodiments, the memory modules 420 may store a threshold intensity for each fluid type as part of the fluid profile for each fluid type. The OFS controller 402 may compare the intensity of IR light measured by the detector 312 to the IR threshold intensities stored in the memory modules 420. An intensity of IR light measured by the detector 312 that is less than the IR threshold intensity stored in the memory modules 420 may indicate the presence of a fluid in the chamber 306. As used herein, a "substantial decrease in intensity" of the IR light refers to a decrease in the intensity of the IR light from the intensity of the IR light emitted from the light source 310 to an intensity of IR light received by the detector 312 that is less than the IR threshold intensity. When a fluid is not present in the chamber 306, the intensity of IR light measured by the detector 312 may be generally the same or only slightly different than the intensity of the IR light emitted by the light source 310 due to the absence of a fluid that absorbs the IR light.

Changes in the temperature of the electronics compartment 372 (FIG. 3) and the light source 310 disposed therein may influence the intensity of the IR light emitted by the light source 310. Additionally, changes in the fluid temperature in the chamber 306 may influence the absorption of IR light by the fluid in the chamber 306. The OFS controller 402 (FIG. 6) may receive a temperature signal from the one or more temperature sensors 430 (FIG. 6) which may be indicative of the temperature of the electronics, fluid temperature, or both. The OFS controller 402 may adjust the intensity of IR light received by the detector 312, the threshold intensity retrieved from the memory modules 420, or both to account for differences in the temperature of the electronics, fluid temperature, or both.

In one or more embodiments, the OFS 130 may use visible light emitted by the light source 310, instead of IR light, to determine whether a fluid is in the chamber 306. The OFS 130 may use one or more specific wavelengths of visible light emitted by the light source 310 to determine whether a fluid is in the chamber 306. In one or more embodiments, the OFS 130 may include a secondary sensor (not shown) for determining whether fluid is present in the chamber 306. In one or more embodiments, the secondary sensor may be a wet-dry sensor.

In one or more embodiments, the OFS 130 may emit IR or visible light into the chamber 306 to determine whether fluid is present in the chamber 306 at periodic time intervals during operation. The OFS controller 402 (FIG. 6) may generate a "fluid present" message when the OFS 130 detects fluid in the chamber 306 and a "no fluid present" message when the OFS 130 does not detect a fluid in the chamber 306. In one or more embodiments, the OFS controller 402 may set a fluid present parameter to a fluid present value or to a no fluid present value and may store the fluid present parameter in the memory modules 420. In embodiments, the system controller 70 (FIG. 6) may query or poll the memory modules 420 of the OFS controller 402 to retrieve the fluid present parameter. In one or more embodiments, the OFS 130 may determine whether fluid is in the chamber 306 as a precondition to emitting visible light or UV light into the chamber 306 for determining a fluid type of the fluid in the chamber 306.

A determination by the OFS 130 that no fluid is present in the chamber 306 may indicate that a storage tank or tank compartment 25 (FIG. 9) is empty of liquid product or that no liquid product is flowing through a transfer pipe or conduit, which may indicate one or more conditions, such as the tank or tank compartment being empty, one or more valves being closed, or other condition. In one or more embodiments, the OFS 130 may be used to provide an indication of when an operation is completed. the OFS 130 may monitor whether fluid is in the chamber 306 throughout an operation, such as unloading the tank compartment 25 (FIG. 9) of a product transport vehicle 15 (FIG. 9) for example, to determine when an operation may be completed or nearing completion. A change in status from a "fluid present" in the chamber 306 status to a "no fluid present" in the chamber 306 status may indicate that a tank compartment is empty or that no more fluid is flowing through the transfer pipe, conduit or control valve. In one or more embodiments, the OFS controller 402 may generate the "no fluid present" message or change the fluid present parameter to a no fluid present value, which may indicate that the operation is complete. The OFS controller 402 may save and/or transmit the fluid present parameter, the "no fluid present" message, or the "fluid present" message to the system controller 70 or to the OFS display 424. In one or more embodiments, the OFS controller 402 may output a fluid present signal indicative of a fluid present in the chamber 306. The fluid present signal indicative of a fluid present in the chamber 306 may be received by the system controller 70. The presence or absence of the fluid present signal may cause the system controller 70 to determine whether a tank is empty or whether an operation, such as a transfer operation is complete.

Referring to FIG. 4B, the OFS 130 may use visible light to determine a fluid type of the fluid in the chamber 306. FIG. 4B schematically illustrates an embodiment of the OFS 130 in which the light source 310 and the detector 312 are positioned at or adjacent to the same side (first side 350) of the chamber 306. The OFS controller 402 (FIG. 6) may send a signal to the light source 310 to cause the light source 310 to emit visible light into the chamber 306. In response, the light source 310 emits the visible light into the chamber 306. The visible light may be emitted by a visible light portion of the light source 310. In one or more embodiments, the light source 310 may include a plurality of visible spectra LEDs, each LED configured to emit a range of wavelengths of visible light. In one or more embodiments, each visible spectra LED may be flashed (i.e., activated for a period of time and then deactivated) in series such that only one wavelength range of visible light is emitted into the chamber 306 at any point in time. The visible light may travel along the optical communication pathway 332, along which the visible light may travel through the fluid in the chamber 306, reflect off of the reflector 330 positioned on the opposite side (second side 352) of the chamber 306, travel back through the fluid in the chamber 306, and is received by the detector 312, which may measure the wavelengths and intensities of the visible light received by the detector 312. The wavelengths and intensities of the visible light may be measured by a visible light portion of the detector 312. FIG. 5B illustrates an embodiment in which the light source 310 is positioned on an opposite side (second side 352) of the chamber 306 from the detector 312. In this arrangement, the visible light emitted by the light source 310 travels along a generally linear path 334 through the fluid in the chamber 306 to the detector 312.

Different types of fluids, such as petroleum-based fuels for example, absorb different wavelengths of visible light passing through the fluid. The visible light that is not absorbed by the fluid may pass through the fluid and reach the detector 312. An intensity of a specific wavelength of visible light measured by the detector 312 that is substantially less than the intensity of that specific wavelength of visible light emitted from the light source 310 may indicate that the fluid in the chamber 306 absorbs that specific wavelength of visible light. Additionally, different types of fluids, such as petroleum-based fuels for example, may reflect different wavelengths of visible light emitted into the fluid. As non-limiting examples, diesel fuels may be slightly amber color or may include a colored dye, which indicates that diesel fuels may reflect yellow wavelengths of light or wavelengths of light associated with the color of the dye, and kerosene may be generally clear or colorless, which may indicate that kerosene reflects very little visible spectra light. Various grades of gasoline may reflect various wavelengths of visible light, which may result in variations in the intensity of specific wavelengths of visible light detected by the detector 312. The visible light reflected by the fluid in the chamber 306 may also be reflected back towards the detector 312 and may contribute to the wavelengths and intensities of the visible light measured by the detector 312. Because each fluid may absorb and reflect different wavelengths of visible light, measurement of the wavelengths and intensities of visible light reaching the detector 312 may provide information on the visible light absorbed and/or reflected by the fluid, which information may provide characteristics with which to identify the fluid type of the fluid in the chamber 306.

The detector 312 may receive the visible light, and the OFS controller 402 may process the wavelength and intensity information for the visible light received by the detector 312 and may compare the wavelength and intensity information for the received visible light to the one or more fluid profiles stored in the one or more memory modules 420. As described previously in this disclosure, the fluid profiles may be in the form of a plurality of LUTs and may include visible light transmissivity profiles for one or more fluids. The OFS controller 402 may determine a fluid type of the fluid in the chamber 306 based on the comparison of the wavelength and intensity of the visible light received by the detector 312 to the plurality of fluid profiles.

Temperature may influence the wavelengths and intensities of visible light emitted by the light source 310. Temperature may also influence the intensities of IR and UV light emitted by the light source 310. As a non-limiting example, the light source 310 may include one or more LEDs, which may experience changes in output brightness with changes in temperature. These changes in LED brightness may then affect the intensity of visible light received by the detector 312. Changes in temperature may also affect the absorption and reflection of visible light by the fluid disposed in the chamber 306, which may also influence the wavelengths and intensities of visible light measured by the detector 312. The OFS controller 402, therefore, may receive a temperature of the electronics, fluid temperature in the chamber 306, or both from one or more temperature sensors 430 and may adjust the wavelength and intensity information determined for the light received by the detector 312 or the fluid profiles stored in the memory modules 420 based on the temperature of the electronics, fluid temperature, or both. In one or more embodiments, the OFS controller 402 may utilize an algorithm stored in the memory modules 420 to mathematically adjust the wavelength and intensity information determined for the light received by the detector, the fluid profiles stored in the memory modules 420, or both to account for changes in the temperature of the electronics, fluid temperature, or both. In one or more embodiments, the memory modules 420 may include a plurality of fluid profiles for each fluid type, each of the plurality of fluid profiles providing the transmissivity profile, fluorescence profile, and other fluid profile information over a range of electronics temperatures, fluid temperatures, or both. The OFS controller 402 may compare the wavelength and intensity information for the light received by the detector 312 to the fluid profiles at a specific temperature, as indicated by the temperature sensors 430. In one or more embodiments, the memory modules 420 may include LUTs of intensity versus temperature for each wavelength of light for each fluid.

Additionally, the OFS controller 402 may use one or more mathematical filters to limit the wavelength and intensity information determined for the light received from the detector 312 to narrower ranges of wavelengths. The mathematical filters enable the OFS controller 402 to focus on specific ranges of wavelength of visible light, which may be expected to provide distinguishing characteristics of the fluid.

In some cases, measurement of the wavelengths and intensities of visible light transmitted through the fluid may not be sufficient to adequately distinguish between two or more different types of fluids. As a non-limiting example, gasoline grades having different octane ratings may absorb and reflect similar wavelengths of visible light such that measuring the wavelengths and intensities of visible light passing through the gasoline grades may not enable the OFS controller 402 to confidently distinguish between the different octane grades of the gasoline. Liquid products, such as different octane grades of gasoline and different grades of diesel fuel for example, may have certain components, such as certain hydrocarbon components or dye components for example, that may fluoresce different wavelengths of visible light when exposed to UV light.

Referring to FIG. 4C, the OFS 130 may measure the wavelengths and intensities of visible light fluoresced by the fluid in the chamber 306 in response to UV light emitted by the light source 310 to further characterize and identify a fluid type of the fluid in the chamber 306. FIG. 4C schematically illustrates an embodiment of the OFS 130 in which the light source 310 and the detector 312 are positioned at or adjacent to the same side (first side 350) of the chamber 306. In one or more embodiments, the OFS 130 may include one or more light sources 310 positioned within the chamber 306. FIG. 4C denotes UV light with reference number 394 and fluoresced visible light by reference number 396. The OFS controller 402 (FIG. 6) may send a control signal to the light source 310 to cause the light source 310 to emit UV light 394 into the chamber 306. In response, the light source 310 emits the UV light 394 into the chamber 306. The UV light 394 may be emitted by a UV portion of the light source 310. In one or more embodiments, the light source 310 does not emit visible light into the chamber 306 simultaneously with emitting the UV light 394.

When a fluid is disposed within the chamber 306, the UV light 394 may travel into the chamber 306 and into the fluid. The UV light 394 may cause the fluid, or one or more components of the fluid, to fluoresce and emit fluoresced visible light 396 into the chamber 306. The fluoresced visible light 396 may be emitted from the fluid in a plurality of directions. A portion of the fluoresced visible light 396 may travel back through the fluid to the detector 312, and another portion of the fluoresced visible light 396 may travel through the fluid, reflect off of the reflector 330, and travel back through the fluid to the detector 312. The fluoresced visible light 396 may be received at the detector 312, which may measure the wavelengths and intensities of the fluoresced visible light 396. The wavelengths and intensities of the fluoresced visible light 396 may be measured by the visible light portion of the detector 312. FIG. 5C illustrates an embodiment in which the light source 310 is positioned at an opposite side (second side 352) of the chamber 306 from the detector 312. In this embodiment, the UV light 394 emitted by the light source 310 travels into the fluid disposed in the chamber 306. Upon exposure to the UV light 394, the fluid, or a component thereof, fluoresced visible light 396, which travels in a plurality of directions. At least a portion of the fluoresced visible light 396 travels towards and is received at the detector 312. The OFS controller 402 may process the received light to determine wavelength and intensity information for the received light.

One or more components of the fluid may fluoresce visible light within one or more specific wavelength ranges when the component is exposed to the UV light 394. Different fluid types may have different components that fluoresce different wavelengths and intensities of fluoresced visible light 396, and these different wavelengths and intensities of fluoresced visible light 396 may provide identifying characteristics for determining the fluid type of the fluid in the chamber 306. As described above, the one or more fluid profiles stored in the memory modules 420 (FIG. 6) may include the fluorescence profiles for the one or more fluids, the fluorescence profiles including wavelengths and intensities of fluoresced visible light 396 expected to be fluoresced by the components in the fluids. The OFS controller 402 may compare the information on the wavelengths and intensities of fluoresced visible light 396 received from the detector 312 to the fluorescence profiles in the one or more fluid profiles to further determine a fluid type of the fluid in the chamber 306. As discussed above, the OFS controller 402 may also adjust the wavelength and intensity information for the fluoresced visible light 396 received by the detector 312 or the fluorescence information in the fluid profiles by the temperature of the electronics, a fluid temperature, or both prior to making the comparison and determining the fluid type of the fluid. In one or more embodiments, the fluid profiles in the memory modules 420 may include fluorescence profiles at various temperatures for each fluid and the OFS controller 402 may select the fluorescence profiles associated with the temperature of electronics, fluid temperature, or both to compare to the information received from the detector 312. As discussed previously, the OFS controller 402 may also utilize one or more mathematical filters to filter the information received from the detector 312 to one or more specific wavelength ranges of visible light expected to be fluoresced by the fluids.

In one or more embodiments, the OFS controller 402 may determine the fluid type of the fluid in the chamber 306 based on the wavelengths and intensities of visible light transmitted through the fluid. In one or more embodiments, the OFS controller 402 may determine the fluid type of the fluid in the chamber 306 based on the wavelengths and intensities of visible light fluoresced by the fluid, or one or more components of the fluid, in response to UV light. In one or more embodiments, the OFS controller 402 may determine the fluid type of the fluid in the chamber 306 based on both the wavelengths and intensities of visible light transmitted through the fluid and the wavelengths and intensities of visible light fluoresced by the fluid, or a component thereof, in response to UV light. In one or more embodiments, the OFS 130 may simultaneously emit IR light and visible light into the chamber 306 to simultaneously determine whether fluid is present in the chamber 306 and measure the wavelengths and intensities of visible light transmitted through the fluid.

Figure 10:
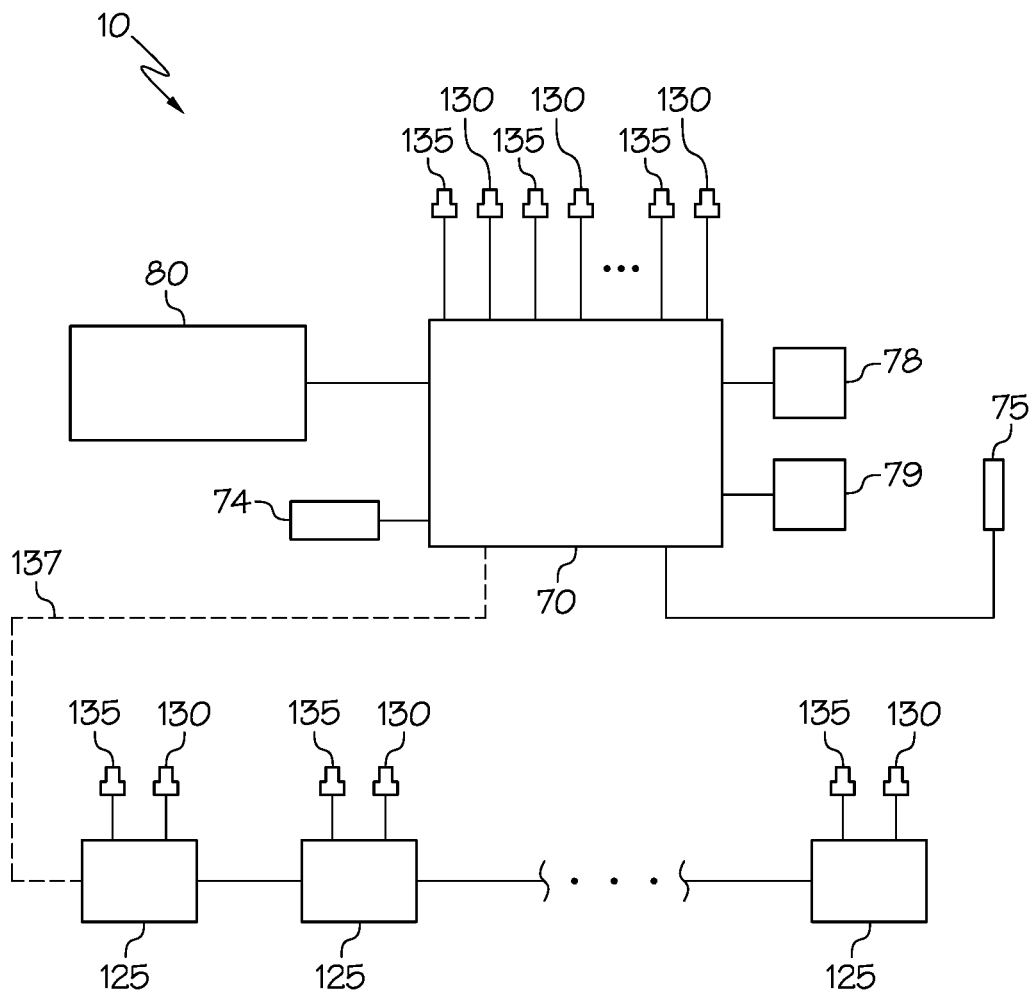
FIG. 10 schematically depicts a crossover protection control system according to one or more embodiments shown and described herein.

Referring back to FIG. 6, once the OFS controller 402 has determined a fluid type of the fluid in the chamber 306, the OFS controller 402 may generate and save a fluid type in the memory modules 420. In one or more embodiments, the OFS 130 may be installed on a product transport vehicle 15 and the fluid type may be a transported liquid type. In one or more other embodiments, the OFS 130 may be installed in a storage tank or distribution tank such that the fluid type may be a stored liquid type. The OFS controller 402 may transmit the fluid type (i.e., as the transported liquid type or stored liquid type depending on where the OFS 130 is installed) to the system controller 70 (FIGS. 6 and 10). In one or more embodiments, the system controller 70 may query or poll the memory modules 420 of the OFS controller 402 to retrieve the fluid type (i.e., as the transported liquid type). In one or more embodiments, the OFS 130 may be configured to output a fluid type signal indicative of a fluid type of the fluid in the chamber 306, and the system controller 70 of the crossover protection system may determine a transported liquid type based on the fluid type signal output from the OFS 130. If the OFS controller 402 is unable to identify the fluid type of the fluid in the chamber based on the visible light transmitted or the visible light fluoresced in response to exposure to UV light, then the OFS controller 402 may generate an "unknown fluid" or "unknown fluid type" message or signal. The OFS controller 402 may save the "unknown fluid" message in the memory modules 420 and/or may transmit the "unknown fluid" message to the system controller 70. In one or more embodiments, the OFS controller 402 may set the fluid type to a value indicative of an unknown fluid type when the OFS controller 402 is unable to determine the fluid type of the fluid in the chamber 306.

The OFS 130 and optical sensor systems 400 disclosed herein may be capable of differentiating between different types of fluids that have similar physical and chemical properties, the similar properties causing the two different types of fluids to be indistinguishable to existing fluid property sensors. In one or more embodiments, the OFS 130 may be capable of distinguishing between different octane grades of gasoline and determining a fluid type for each separate grade. In one or more embodiments, the OFS 130 may be capable of distinguishing between different grades of dyed diesel fuels. The OFS 130 may be capable of distinguishing between a wide range of fluids that are liquids, such as petroleum-based fuels (e.g., diesel fuel, gasoline, and kerosene), organic solvents, resins, aqueous solutions, or other materials. In one or more embodiments, the OFS 130 may be capable of distinguishing between one or more fluids that are vapors or gases. In one or more embodiments, the OFS 130 may also be capable of indicating when a tank is empty or when an operation, such as a material transfer operation, is complete.

Figure 7:
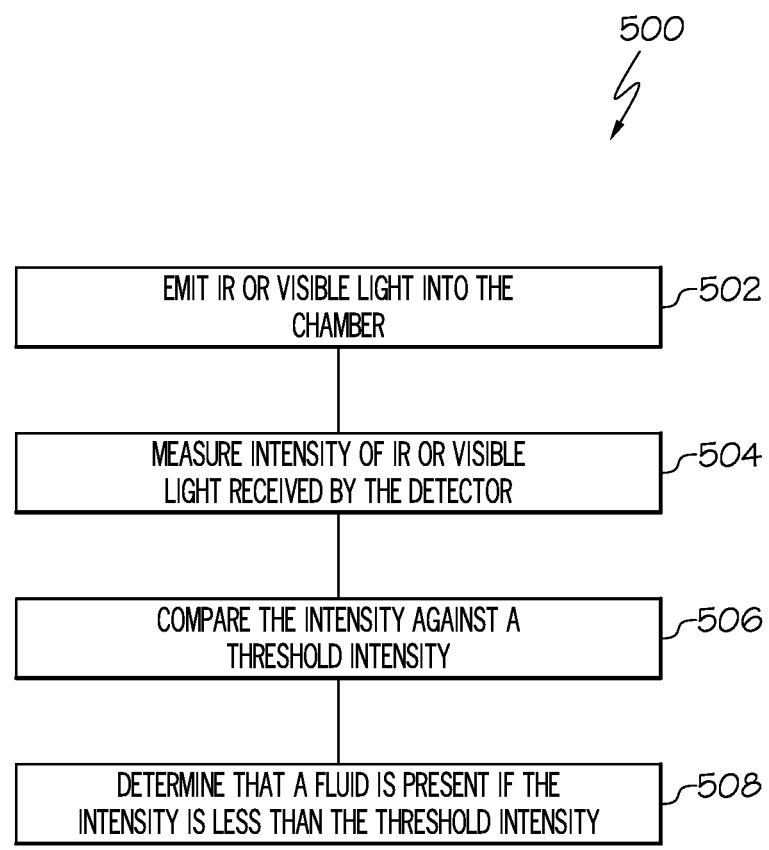
FIG. 7 schematically depicts a flowchart of a method for determining whether a fluid is present in the optical fluid sensor, according to one or more embodiments shown and described herein.
Figure 8:
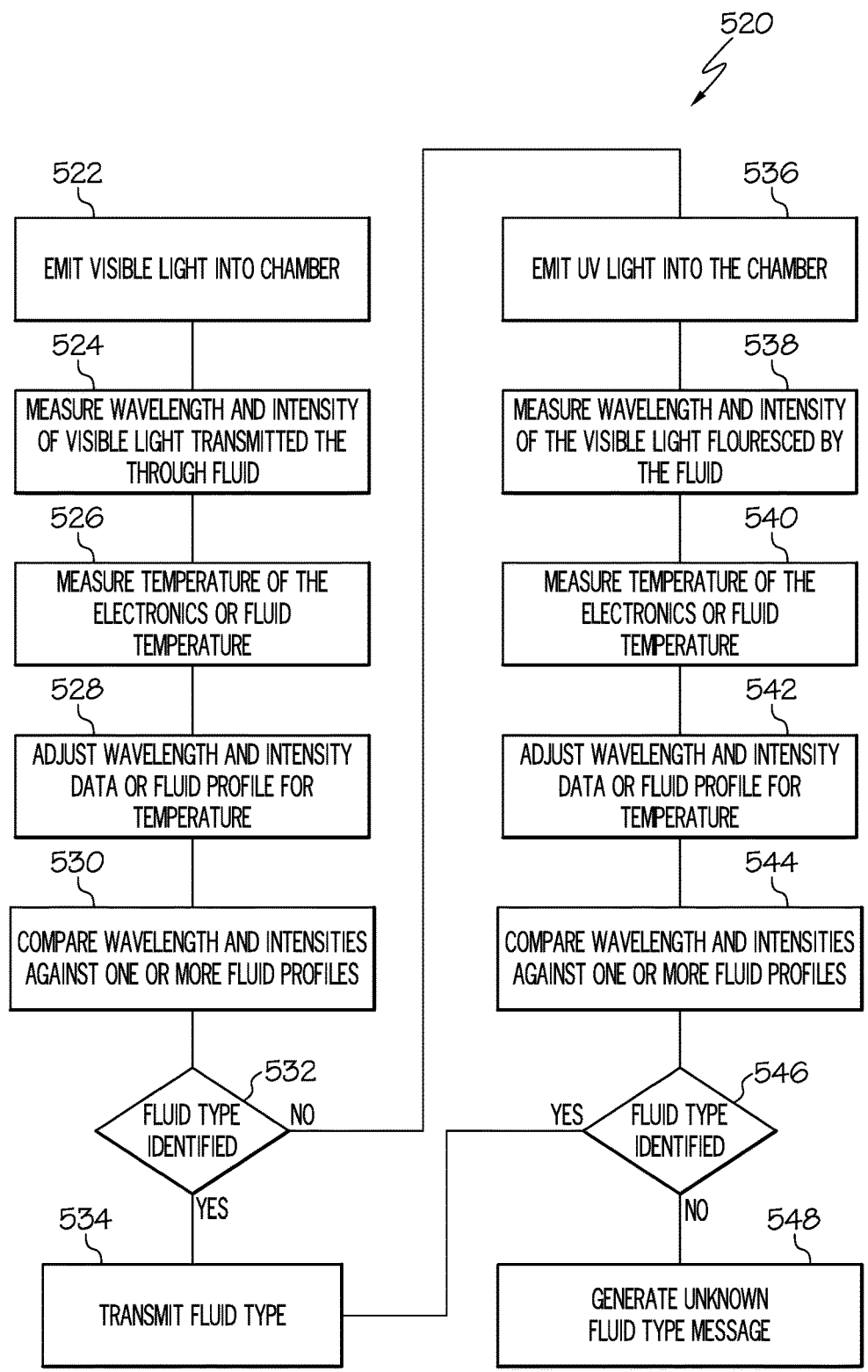
FIG. 8 schematically depicts a flowchart of a method for determining a fluid type of a fluid using the optical fluid sensor, according to one or more embodiments shown and described herein.

Referring now to FIGS. 7-8, a method 500 for determining whether a fluid is present in the chamber 306 and a method 520 for determining a fluid type of a fluid in the chamber 306 are schematically depicted. Although the steps associated with the blocks of FIGS. 7-9 will be described as being separate tasks, in other embodiments, the blocks may be combined or omitted. Further, while the steps associated with the blocks of FIGS. 7-8 will be described as being performed in a particular order, in other embodiments, the steps may be performed in a different order. The machine readable instructions recited in the following discussion may be stored on the memory modules 420 and may be executed by the processor 410.

Referring to FIG. 7, the method 500 for determining whether a fluid is present in the chamber 306 of the OFS 130 is schematically depicted. At block 502, machine readable instructions stored on the one or more memory modules 420, when executed by the processor 410, may cause the OFS 130, in particular the OFS controller 420, to transmit a control signal to the light source 310 to cause the light source 310 to emit IR light or visible light into the chamber 306. In response to the control signal, the light source 310 may emit IR light or visible light into the chamber 306. In one or more embodiment, the control signal may instruct the light source 310 to emit IR light or visible light. In one or more embodiments, the OFS controller 402 may cause the light source 310 to emit IR light into the chamber 306. The machine readable instructions may cause the OFS 130 to receive IR light or visible light at the detector 312.

At block 504, the machine readable instructions, when executed, may cause the OFS 130 to measure an intensity of the IR or visible light received at the detector 360. In one or more embodiments, the machine readable instructions may cause the OFS 130 to receive IR or visible light at the detector. The OFS controller 402 may process the IR light or visible light received at the detector to determine an intensity of IR or visible light received by the detector 312. The OFS controller 402 may save the intensity of IR or visible light information in the one or more memory modules 420. The machine readable instructions, when executed, may cause the OFS controller 402 to apply a mathematical filter to IR or visible light received at the detector 312.

In block 506, the machine readable instructions, when executed, may cause the OFS controller 402 to compare the intensity of the received IR light or visible light to a threshold intensity of IR light or visible light, respectively. The processor 410 may query the memory modules 420 to retrieve the threshold intensity, which may be stored in the memory modules 420 in one or more LUTs. The machine readable instructions, when executed, may cause the OFS controller 402 to adjust the wavelength and intensity information for the received IR or visible light or the threshold intensity retrieved from the memory modules 420 based on the temperature of the electronics, the fluid temperature, or both. In block 508, the machine readable instructions, when executed, may cause the OFS controller 402 to determine that a fluid is present if the intensity of the received IR light or visible light is less than the threshold intensity of IR light or visible light. The OFS controller 402 may generate a "fluid present" or "no fluid present" message or set a fluid present parameter to a fluid present value or a no fluid present value to indicate whether a fluid is present in the chamber 306.

Referring now to FIG. 8, the method 520 for determining a fluid type of the fluid in the chamber 306 is schematically depicted. In block 522, machine readable instructions, when executed, may cause the OFS controller 402 to send or transmit a control signal to the light source 310 to cause the light source 310 to emit visible light into the chamber 306. In response to the control signal, the light source 310 may emit visible light into the chamber 306. In block 524, the machine readable instructions, when executed, may cause the OFS controller 402 to receive wavelength and intensity information for visible light received by the detector 312. The wavelength and intensity information may be received from the detector 312 through the communicative coupling of the detector 312 to the OFS controller 402. In one or more embodiments, the OFS controller 402 may receive one or more signals indicative of wavelengths and intensities of visible light received at the detector 312 from the detector 312 and may process the signal from the detector 312 to determine the wavelengths and intensities of received visible light. The wavelength and intensity information for the received light may be saved in the one or more memory modules 420.

In block 526, the machine readable instructions, when executed, may cause the OFS controller 402 to receive a temperature signal from the temperature sensor 430. In embodiments, the temperature sensor 430 may be positioned in the electronics compartment 372 such that the temperature signal may indicate a temperature of the electronics. In other embodiments, the temperature sensor 430 may be positioned in the chamber 306 such that the temperature signal may indicate a fluid temperature in the chamber 306. In other embodiments, the OFS controller 402 may receive a first temperature signal from a temperature sensor 430 in the electronics compartment 372 and a second temperature signal from another temperature sensor 430 positioned in the chamber 306. In block 528, the machine readable instructions, when executed, may cause the OFS controller 402 to adjust one or more fluid profiles stored in the memory modules 420 or the wavelength and intensity information received from the detector 312 based on one or more temperature signals. To adjust the fluid profiles for temperature, the processor 410 may query the memory modules 420 to retrieve one or more of the fluid profiles, which are stored in the memory modules 420. In one or more embodiments, the OFS controller 402 may adjust both the fluid profiles and the wavelength and intensity information received from the detector 312 for changes in temperature.

In block 530, the machine readable instructions, when executed, may cause the OFS controller 402 to compare the wavelength and intensity information for the received visible light, which was received by the detector 312, to the one or more fluid profiles stored in the one or more memory modules 420. The OFS controller 402 may determine a fluid type of the fluid in the chamber 306 based on the comparison of the wavelength and intensity information for the received visible light to the one or more fluid profiles. The machine readable instructions, when executed, may cause the OFS controller 402 to query the memory modules 420 to retrieve one or more fluid profiles. In block 532, the machine readable instructions, when executed, may cause the OFS controller 402 to determine whether a fluid type is successfully identified by the OFS controller 402. If the OFS controller 402 determines that it has successfully identified a fluid type of the fluid, the machine readable instructions, when executed, may cause the OFS controller 402 to generate and transmit a liquid type, which is indicative of the fluid type of the fluid in the chamber 306, to the system controller 70 and/or the OFS display 424. In one or more embodiments, the OFS 130 may be positioned in contact with a tank compartment 25 (FIG. 9) or control valve 45 (FIG. 9) of a product transport vehicle 15 (FIG. 9) such that the liquid type may be a transported liquid type. In one or more embodiments, the OFS 130 may output a fluid type signal indicative of the fluid type, and the system controller 70 may receive the output from the OFS 130. If the OFS controller 402 determines that it has not determined the fluid type of the fluid in the chamber 306, then the OFS controller 402 may generate and transmit an "unknown fluid type" message to the system controller 70 or may proceed with measuring the UV fluorescence of the fluid in the chamber 306 (i.e., proceed to block 536 of method 520) to further determine the fluid type.

In block 536, the machine readable instructions, when executed by the processor 410, may cause the OFS controller 402 to send a control signal to the light source 310 to cause the light source 310 to emit UV light into the chamber 306. In response to the control signal, the light source 310 may emit UV light into the chamber 306. In block 538, the machine readable instructions, when executed, may cause the OFS controller 402 to receive wavelength and intensity information for visible light fluoresced by the fluid (fluoresced visible light 396) and received by the detector 312. The wavelength and intensity information may be received from the detector 312 through the communicative coupling of the detector 312 to the OFS controller 402. In one or more embodiments, the OFS controller 402 may receive the wavelengths and intensities of the received light directly from the detector 312. In other embodiments, the OFS controller 402 may receive one or more signals indicative of wavelengths and intensities of visible light received at the detector 312 and may process the one or more signals from the detector 312 to determine the wavelengths and intensities of visible light received by the detector 312. The wavelength and intensity information for the received visible light may be saved in the one or more memory modules 420.

In block 540, the machine readable instructions, when executed, may cause the OFS controller 402 to receive a temperature signal from the temperature sensor 430. As described previously, the temperature signal may indicate the temperature of the electronics, the fluid temperature in the chamber 306, or both. In one or more embodiments, OFS controller 402 may use the temperature signal(s) from block 526 rather than receiving another temperature signal in block 540. In block 542, the machine readable instructions, when executed, may cause the OFS controller 402 to adjust one or more fluid profiles stored in the memory modules 420 or the wavelength and intensity information for the fluoresced visible light 396 received from the detector 312 based on the one or more temperature signals. The one or more temperature signals may be from block 526 or block 540. To adjust the fluid profiles for temperature, the processor 410 may query the memory modules 420 to retrieve one or more of the fluid profiles, which are stored in the memory modules 420. In one or more embodiments, the OFS controller 402 may adjust both the fluid profiles and the wavelength and intensity information received from the detector 312 for changes in temperature.

In block 544, the machine readable instructions, when executed, may cause the OFS controller 402 to compare the wavelength and intensity information for the fluoresced visible light 396 received from the detector 312 to the one or more fluid profiles stored in the one or more memory modules 420 to determine a fluid type of the fluid in the chamber 306. Each of the one or more fluid profiles may comprise information on one or more fluorescent properties of the fluid (e.g., fluorescence profiles). The machine readable instructions, when executed, may cause the OFS controller 402 to query the memory modules 420 to retrieve the one or more fluid profiles. The OFS controller 402 may compare the wavelength and intensity of the fluoresced visible light 396 to the one or more fluid profiles retrieved from the memory modules 420. The OFS controller 402 may determine a fluid type of the fluid in the chamber 306 based on the comparison of the wavelength and intensity of the fluoresced visible light 396 to the one or more fluid profiles. In block 546, the machine readable instructions, when executed, may cause the OFS controller 402 to determine whether a fluid type is successfully identified by the OFS controller 402. Referring to block 534, if the OFS controller 402 determines that is has successfully identified a fluid type of the fluid, the machine readable instructions, when executed, may cause the OFS controller 402 to generate and transmit a liquid type, which is indicative of the fluid type of the fluid in the chamber 306, to the system controller 70 and/or the OFS display 424. In one or more embodiments, the OFS 130 may be positioned in contact with a tank compartment 25 (FIG. 9) or control valve 45 (FIG. 9) of a product transport vehicle 15 (FIG. 9) such that the liquid type may be a transported liquid type. In one or more embodiments, the OFS controller 402 may generate an output signal indicative of a fluid type of the fluid in the chamber 306, and the system controller 70 may use the output from the OFS controller 402 to determine a transported liquid type. Referring to block 548, if the OFS controller 402 has not determined the fluid type of the fluid in the chamber 306, then the OFS controller 402 may generate an "unknown fluid type" message and transmit the "unknown fluid type" message to the system controller 70.

Although FIG. 8 depicts method 520 as emitting visible light into the chamber 306 first and then emitting UV light second, in one or more embodiments, the machine readable instructions, when executed, may cause the OFS controller 402 to emit UV light into the chamber 306 first and compare the wavelength and intensity of fluoresced visible light 396 received by the detector 312 to the fluid profiles before emitting visible light into the chamber 306 and measuring the wavelength and intensity of visible light transmitted through the fluid in the chamber 306. In one or more embodiments, the OFS controller 402 may operate to determine whether a fluid is in the chamber 306, to determine a fluid type of the fluid in the chamber 306, or both in response to receiving a control signal from the system controller 70. In one or more embodiments, the OFS controller 402 may determine whether fluid is present in the chamber 306, according to method 500, at periodic time intervals. In one or more embodiments, the OFS controller 402 may determine that a fluid is present in the chamber 306 before executing the machine readable instructions to determine a fluid type of the fluid in the chamber 306.

In one or more embodiments, the machine readable instructions stored on the one or more memory modules 420 may cause the OFS 130 to perform at least the following when executed by processor 410: transmit a control signal to the light source 310 to cause the light source 310 to emit visible light into the chamber 306; receive visible light at the detector 312; process the received light to determine wavelength and intensity information for the received light; compare the wavelength and intensity information for the received visible light to one or more fluid profiles stored in the one or more memory modules 420; and determine a fluid type of the fluid in the chamber 306 based on the comparison of the wavelength and intensity information for the received visible light to the one or more fluid profiles.

In one or more embodiments, the machine readable instructions stored on the one or more memory modules 420 may cause the OFS 130 to perform at least the following when executed by processor 410: transmit a control signal to the light source 310 to cause the light source 310 to emit UV light into the chamber 306 in order to cause the fluid to fluoresce visible light; receive visible light at the detector 312; process the received light to determine wavelength and intensity information for the received light; compare the wavelength and intensity information for the received light to one or more fluid profiles stored in the one or more memory modules 420, wherein each of the one or more fluid profiles comprises information on one or more fluorescent properties of the fluid; and determine a fluid type of the fluid in the chamber 360 based on the comparison of the wavelength and intensity information for the received light to the one or more fluid profiles.

As previously discussed, the OFS 130 may be incorporated into a crossover protection system for preventing co-mingling of dissimilar liquid products during material transfer operations. Referring to FIG. 9, a crossover protection system may include a product transport vehicle comprising a tank compartment for containing a liquid product and a valve coupled to the tank compartment, the valve regulating a flow of liquid product from the tank compartment. The valve may have a normally locked state. The crossover protection system may have an OFS as disclosed hereinabove positioned to contact the liquid product stored in the tank compartment. The crossover protection system may also include a tank delivery connector fluidly coupled to a distribution side of the valve. The tank delivery connector may comprise a tank tag reader for interrogating a tank tag coupled to a distribution tank separate from the product transport vehicle to retrieve a stored liquid type encoded on the tank tag. The stored liquid type is indicative of a fluid type of the liquid product (fluid) in the distribution tank. The crossover protection system may further comprise a system controller communicatively coupled to the valve, the optical fluid sensor, and the tank delivery connector. The system controller may comprise a processor and one or more memory modules communicatively coupled to the processor. The crossover protection system may further include machine readable instructions stored in the one or more memory modules that cause the sensor to perform at least the following when executed by the processor: receive a transported liquid type from the optical fluid sensor; receive the stored liquid type signal transmitted by the tank delivery connector; determine the stored liquid type based on the stored liquid type signal; compare the transported liquid type to the stored liquid type; maintain the valve in the normally locked state when the stored liquid type and the transported liquid type do not match to prevent the flow of liquid product from the tank compartment; and transition the valve from the normally locked state to an unlocked state when the stored liquid type and the transported liquid type match, thereby permitting the flow of liquid product from the tank compartment.

Figure 15:
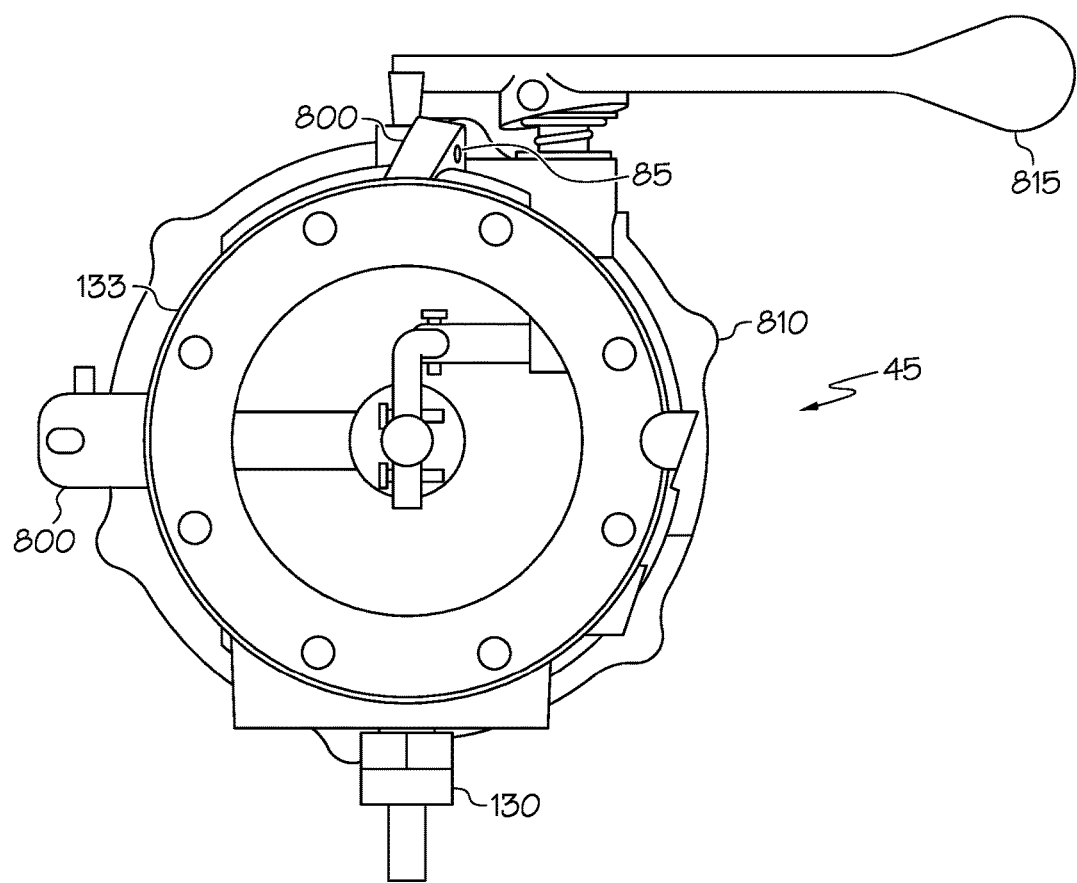
FIG. 15 is a front view of a control valve according to one or more embodiments shown and described herein.

Referring to FIG. 9, a product transport vehicle 15 at a distribution station 20 is schematically depicted. The product transport vehicle 15 may be used to transport liquid product between two points, such as between a fuel depot and retail distribution station 20. For example, the product transport vehicle 15 may be a tanker truck used to transport fuel products between the fuel depot (shown in FIG. 12) and the distribution station 20. The product transport vehicle 15 may have a plurality of tank compartments 25 for containing liquid product, where each tank compartment 25 may have a manlid 30 and a hose adaptor assembly 35. Each hose adaptor assembly 35 may include an emergency valve 40 fluidly coupled to the bottom of the tank compartment 25, a control valve 45, and a pipe connection 50 fluidly coupling the emergency valve 40 to the control valve 45. An example of a suitable emergency valve 40 is the MaxAir series of internal valves by Civacon. An example of a suitable control valve 45 is the API Adaptor, model number 891BA-LK by Civacon. However, it should be understood that alternative valves may be used. A hose adaptor 133 may be coupled to the control valve 45 or the pipe connection 50. In some embodiments, the control valve 45 and the hose adaptor 133 are a single assembly as shown in FIGS. 15 and 16 and described in greater detail herein. An example of a suitable hose adaptor 133 is the gravity coupler, model number 871 or 876 by Civacon. However, it should be understood that alternative hose adaptors may be used. In embodiments, the hose adaptor assembly 35 may include both the emergency valve 40 and the control valve 45 as shown in FIG. 9. Alternatively, the hose adaptor assembly 35 may only include either the emergency valve 40 or the control valve 45. The individual valves (control valve 45 and/or emergency valve 40) of the plurality of valves regulate the flow of liquid product into and out of the corresponding tank compartment 25. A delivery hose 55 may be used to fluidly couple the hose adaptor 133 to a tank delivery connector 60. The tank delivery connector 60, in turn, may be used to fluidly couple the tank compartment 25 with a distribution tank 65 located at the distribution station 20. The tank delivery connector 60 may be removably coupled to the delivery hose 55 and the distribution tank 65.

In the embodiments described herein, at least one of the control valve 45 and the emergency valve 40 has a normally locked state. The phrase "normally locked state" means that the system controller 70 (described in further detail herein) coupled to the valve (e.g. the emergency valve 40 and/or the control valve 45) maintains the valve in a closed and locked position and that the valve can only be unlocked upon confirmation of a match between a stored liquid type and a transported liquid type contained in a corresponding tank compartment 25. When a match is confirmed, the system controller 70 transitions the valve corresponding to a tank compartment 25 with the same product to an unlocked state. In the unlocked state, the valve can be opened or closed by an operator either manually or through the system controller, thereby facilitating the unloading of the transported liquid product contained in the corresponding tank compartment 25.

Referring now to FIGS. 9-11, the crossover protection system 10 may further include a system controller 70 and a tank tag reader 95 for interrogating a tank tag 110 coupled to a distribution tank 65, such as an underground storage tank or similar storage tank. The crossover protection system 10 may include the OFS 130, a pressure sensor 135, a controller antenna 75, an accelerometer 78 for determining when the product transport vehicle is in motion or stationary, a wireless communication module 74, one or more input devices (not shown) such as a keypad or the like, a solenoid valve assembly to pneumatically control the plurality of valves (described in greater detail herein), a display 80, a computer-readable medium (such as a memory or the like), and a processor. In some embodiments, the crossover protection system 10 may further comprise a parking brake sensor 79 communicatively coupled to the processor. The parking brake sensor 79 may be utilized to determine when the product transport vehicle 15 is parked such that a loading or unloading operation may be initiated.

The system controller 70 may be communicatively coupled to the OFS 130 and the pressure sensor 135. An example of a suitable pressure sensor is the diaphragm pressure sensor, model number 1E/F by Televac. However, it should be understood that alternative pressure sensors may be used, such as, for example, a piezo pressure sensor or an electric pressure sensor. It is contemplated that the OFS 130 and the pressure sensor 135, if both are installed on the product transport vehicle 15, may be installed in the same location or at separate locations. For example both the OFS 130 and the pressure sensor 135 may be coupled to the tank compartment 25. Alternatively, the OFS 130 and/or the pressure sensor 135 may be coupled to the pipe connection 50. The OFS 130 may be positioned in the pipe connection 50 such that the OFS 130 is able to interact with liquid product flowing through the pipe connection 50, thereby allowing the system controller 70 to discriminate between different liquid products, such as between different octane-grades of gasoline, dyed diesel types, organic solvents, aqueous solutions, resins, and other liquid products.

The crossover protection system 10 may also include one or more fluid property sensors (not shown) in addition to the OFS 130. An example of a suitable fluid property sensor may be the tuning fork sensor model number FPS2800B12C4 by Measurement Specialties. However, it should be understood that alternative sensors may be used. In one or more embodiments, the fluid property sensor may be located in the tank compartment 25 and positioned to contact liquid product stored in the tank compartment.

The processor of the system controller 70 may be used to execute a set of instructions recorded on the computer-readable medium to prevent the cross contamination of product stored in the distribution tank 65 with dissimilar product stored in one or more of the tank compartments 25 of the product transport vehicle 15. The processor may be communicatively coupled to the controller antenna 75, accelerometer 78, wireless communication module 74, one or more input devices, the display 80, and the computer-readable medium. The system controller 70 may be powered by 12 volt direct current (VDC) or 24 VDC power or a portable power source such as a battery source and/or a solar cell, for example. The display 80 may be an alphanumeric display that presents information, such as system status or the like, to the operator. The display 80 may be positioned anywhere on the product transport vehicle 15 and may be electrically coupled to the system controller 70. For example, in one embodiment, the display 80 is wirelessly coupled to the system controller 70 and is positionable and relocatable on the product transport vehicle 15. In embodiments, status information displayed on the display 80 may include which tank compartments 25 are empty or have some amount of liquid product in them as indicated by the plurality of pressure sensors 135. In embodiments, status information may also include the transported liquid type associated with each tank compartment 25 as sensed and determined by an OFS 130, which communicates the transported liquid type to the system controller 70. Further, status information may also include the stored liquid type of the liquid product stored in a distribution tank 65. In addition to the transported liquid type of the liquid product in each tank compartment 25, other information related to the crossover protection system 10 may also be presented, including, without limitation, battery life remaining, any fault codes, and/or tank tag identification information. The display 80 may include a schematic diagram of the product transport vehicle 15 indicating the status of the tank compartments 25 and schematically depicting fluid flow while in operation. In embodiments, the display 80 may be a touch screen. The keypad or plurality of input devices may include north, south, east, west arrow navigation keys, an enter key, an override key, and/or a numeric keypad.

The system controller 70 may include a set of communication ports (not shown) to communicatively connect to the wireless communication module 74, or to an in-cab black box (not shown) where the processor, computer-readable medium, an onboard overfill detection system (not shown), and other components that may reside on the product transport vehicle 15. A local power port (not shown) may be included to provide power to the system controller 70 in the event the power source failure or battery source failure/depletion. The system controller 70 may be connected to other devices, such as the OFS 130, for example, by wired, wireless, and/or optical communications. A communication port may be included to communicatively connect to other devices using RS-485 protocol, CANbus protocol J1939, CAN open, or a similar protocol, and a 6-pin cable. The tank tag reader 95 may be communicatively coupled to the system controller 70 with electrical wires (not shown) or wirelessly utilizing standard wireless communication protocols. Suitable wireless communication protocols may include the 802.11 families of protocols, the Bluetooth® protocol, the ZigBee IEEE 802 Standard protocol, or the like. In some embodiments, the system controller 70 may wirelessly communicate with the tank tag reader 95 via a pair of antennas, for example the controller antenna 75 and/or the tank connector antenna 115. Additionally, the system controller 70 may also be communicatively coupled to a LAN or WAN through one or more Ethernet cables or wireless Ethernet connections.

The system controller 70 may log and time stamp all events as they occur within the crossover protection system 10. For example, the system controller 70 may log trip records, stored liquid type, transported liquid type, tank compartment usage, amount of liquid product loaded and unloaded, and similar events. The system controller log may be downloaded and used to reconstruct trip events with a computer. In embodiments, the computer-readable medium (i.e., memory) may be large enough to hold either an estimated 30 days worth of trip logs. Alternatively or additionally, the computer-readable medium may be large enough to hold an estimated 200 trip logs. In some embodiments, the in-cab black box may be communicatively connected to an on-truck computer (not shown) to enable the logs to be uploaded to a remote computer system wirelessly through the on-product transport vehicle communication systems.

Referring specifically to FIG. 10, the crossover protection system 10 is schematically depicted as it relates to components on the product transport vehicle 15 of FIG. 9. The system controller 70 may receive a transported fluid type from the OFS 130. The system controller 70 may optionally receive a fluid property signal from an optional fluid property sensor supplemental to the OFS 130, the fluid property signal indicative of at least one of a viscosity of the liquid product in the tank compartment 25, a density of the liquid product in the tank compartment 25, a dielectric constant of the liquid product in the tank compartment 25, and a temperature of the liquid product in the tank compartment 25. In some embodiments, the system controller 70 may include a liquid type LUT stored in memory. The LUT may contain a plurality of liquid types indexed according to one or more fluid properties at a specified temperature or temperatures. These properties may include the viscosity, density, dielectric constant, or combinations thereof. Using this LUT, the system controller 70 may verify the transported liquid type received from the OFS 130 by comparing the transported liquid type from the OFS 130 against a liquid type indicated by the fluid property signal received from the fluid property sensor.

As noted hereinabove, the pressure sensor 135 may be positioned in either the pipe connection 50 or the tank compartment 25 such that the pressure sensor 135 is able to detect the pressure of the liquid product within the pipe connection 50 and the tank compartment 25, thereby allowing the system controller 70 to detect static pressure in the tank compartment 25 and gauge the approximate level or amount of product in the tank compartment 25. The PGI controller 125 may also display the amount of liquid product remaining in the tank compartment 25 as determined by the pressure sensor 135. In another embodiment, the system controller 70 may display the amount of liquid product remaining in the tank compartment 25 as determined by the pressure sensor 135 on the display 80. The system controller 70 may receive a pressure signal from the pressure sensor 135. The pressure signal may indicate the amount of liquid product present in the tank compartment 25. The system controller 70 may display the transported liquid type obtained from the OFS 130 and/or the amount of liquid product indicated by the pressure signal on the display 80 of FIG. 9.

The system controller 70 may also receive an accelerometer signal from the accelerometer 78. The accelerometer signal may indicate whether the product transport vehicle 15 is in motion or not. The system controller 70 may use the accelerometer signal to either maintain the valves in the normally locked state while the product transport vehicle 15 is in motion or transition the valves to the normally locked state when the accelerometer 78 indicates that the product transport vehicle 15 has started to move.

Still referring to FIG. 10, in some embodiments, one or more PGI controllers 125 may be communicatively coupled with the plurality of OFS 130 and the plurality of pressure sensors 135. In embodiments, individual PGI controllers 125 may be associated with a specific hose adaptor assembly 35 and/or associated tank compartment 25 and may be used in conjunction with the system controller to regulate the flow of fluid to and from each tank compartment. However, it should be understood that the PGI controllers are optional and that in some embodiments the crossover protection system 10 does not utilize PGI controllers.

Figure 11A:
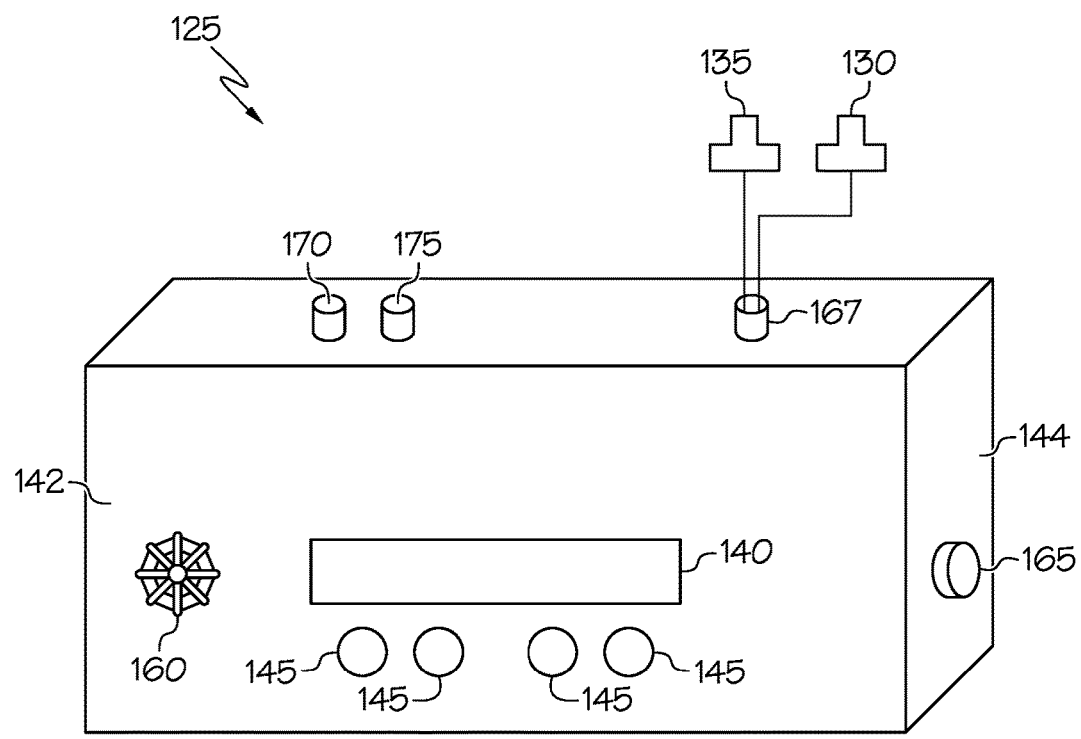
FIG. 11A schematically depicts an electronic product grade indicator controller according to one or more embodiments shown and described herein.

Referring now to FIG. 11A, an embodiment of a PGI controller 125 is schematically depicted. Each PGI controller 125 of the plurality of PGI controllers is associated with a tank compartment 25 of the plurality of tank compartments. The PGI controller 125 may have a computer-readable medium (i.e., a memory) and a processor to execute a set of instructions recorded on the computer-readable medium. The processor may be communicatively coupled to a PGI display 140, a plurality of input devices 145, an alert device, a solenoid valve assembly to pneumatically control the valves corresponding to the tank compartment 25 the PGI controller 125 is associated with, a pressure switch 155, a loading arm sensor (loading arm proximity/detection sensor) input and the computer-readable medium. The PGI display 140, such as a liquid crystal display or a similar electronic display, is mounted to a PGI face 142 of the PGI controller 125. The plurality of input devices 145 may also be mounted to the PGI face 142 of the PGI controller 125 to allow an operator to interact with the PGI controller 125 and enter liquid product identification information into the PGI controller 125. The plurality of input devices 145 and the PGI display 140 allow an operator to choose the liquid product type that is being loaded into the tank compartment 25 to which the PGI controller 125 is associated. For example, the plurality of input devices 145 may be buttons to allow the operator to scroll up and down through a list of liquid product types stored in a computer readable medium of the PGI controller 125 and displayed on the PGI display 140. The input devices 145 allow the operator to make a selection from the list or, alternatively, to directly input liquid product information into the PGI controller 125 identifying the contents of the tank compartment 25 of the product transport vehicle 15. In some embodiments, the PGI controller 125 may include an "empty" input device which allows the operator to quickly indicate the tank compartment 25 is empty. The plurality of input devices 145 may include, without limitation, a keypad, scroll wheel, touchpad, or any other suitable input device that enables an operator to interact with the PGI controller 125. In some embodiments, an audio device 160 may be mounted to the face of the PGI controller 125 and may provide an audible signal to draw the attention of the operator to the PGI controller 125.

A PGI connector 165 may be connected to a PGI body 144 to electrically couple the plurality of PGI controllers 125 together and to electrically couple the plurality of PGI controllers 125 to the system controller 70. A sensor connector 167 may be connected to the PGI body 144 to electrically couple the pressure sensor 135 to the PGI controller 125 and/or communicatively couple the OFS 130 to the PGI controller 125. An air input connector 170 and an air output connector 175 for use by a PGI pneumatic system 180 as shown in FIG. 11B may also be mounted to the PGI body 144.

Figure 11B:
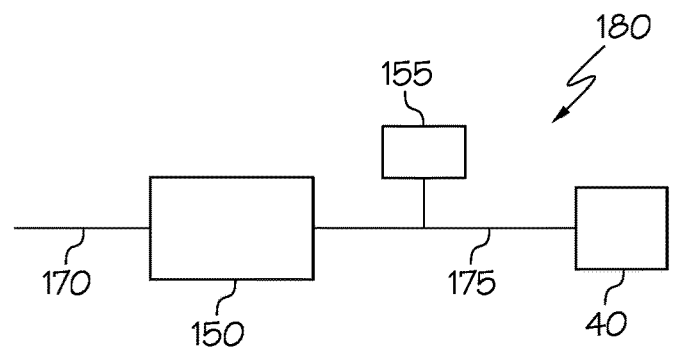
FIG. 11B schematically depicts a product grade indicator pneumatic system according to one or more embodiments shown and described herein.

Referring now to FIGS. 10, 11A, and 11B, FIG. 11B is a schematic view of the PGI pneumatic system 180. The PGI pneumatic system 180 may be coupled to the hose adaptor assembly 35 (FIG. 9), the emergency valve 40 and/or the control valve 45 (FIG. 9). FIG. 11B depicts the PGI controller coupled to the emergency valve 40. The PGI pneumatic system 180 either maintains the valve to which it is connected in the normally locked state and transitions the valve from the normally locked state to an unlocked state based on instructions received from the PGI controller 125 (FIG. 11A) and/or the system controller 70 (FIG. 10). The solenoid valve assembly 150 and the pressure switch 155 of the PGI pneumatic system may be mounted internal to the PGI controller 125 or the system controller 70 (FIG. 10). Referring to FIGS. 11A and 11B, pressurized air may be fed into the solenoid valve assembly 150 through the air input connector 170 on the PGI body 144 or a system controller body (not shown). When the PGI controller 125 or system controller 70 (FIG. 10) opens the solenoid valve assembly 150, the pressurized air actuates the pressure switch 155 and transitions the valve from the normally locked state to the unlocked state thereby allowing liquid product to flow out of the tank compartment 25 (FIG. 9). The PGI pneumatic system 180 delivers pressurized air to the valve using the air output connector 175. In embodiments, the solenoid valve assembly 150 may be manually opened by the operator activating a valve manual override input device on the PGI controller 125 or the system controller 70. In some embodiments, the solenoid valve assembly 150 may be a normally locked solenoid valve. Based on the foregoing, it should be understood that the PGI pneumatic system 180, whether contained in the PGI controller 125 or the system controller 70 (FIG. 10), may control the locking/unlocking of the corresponding valve as well as the opening and closing of the corresponding valve to allow or prevent fluid flow.

While the PGI pneumatic system has been described herein as being coupled to or a part of the PGI controller, in some embodiments, the system controller 70 (FIG. 10) may incorporate all the functions of the plurality of PGI controllers 125. In these embodiments, the system controller 70 includes the PGI pneumatic system 180 for each valve on the product transport vehicle 15. For example, all the solenoid valve assemblies 150 may be combined together in a manifold arrangement and mounted in a separate location and electrically coupled to the system controller 70. In these embodiments, the system controller 70 may also include the plurality of input devices 145, and alert devices. This would eliminate the need for a plurality of PGI controllers 125 and associated equipment.

Referring to FIG. 10, in embodiments, the PGI controller 125 may be used by an operator to manually enter the transported liquid type into the system controller 70. The transported liquid type from the OFS 130 and/or the pressure signal from the pressure sensor 135 may also be received by an individual PGI controller 125. The PGI controller 125 may be communicatively coupled with the system controller 70 and may transmit the transported liquid type and/or the pressure signal to the system controller 70 for processing by the processor. The transported fluid property type signal from the optional fluid property sensor may also be received by an individual PGI controller 125 and transmitted on to the system controller 70. The PGI controller 125 may also display the transported liquid type received from the OFS 130 and/or the amount of liquid product indicated by the pressure signal on the PGI display 140 (FIG. 11A).

The operator may override the system controller 70 using the plurality of input devices 145 on the PGI controller 125 or on the system controller 70. A log of any override action taken by the operator may be stored in the system controller 70 memory for later retrieval and analysis.

In some embodiments, each PGI controller 125 may be communicatively coupled to another PGI controller 125 as shown in FIG. 10 or multiple PGI controllers 125, and at least one of the PGI controllers 125 is coupled to the system controller 70. Alternatively, each PGI controller 125 may be directly coupled to the system controller 70. In one embodiment, a total of twelve PGI controllers 125 may be communicatively coupled to the system controller 70 with a six-pin cable 137, such as when the product transport vehicle 15 (shown in FIG. 9) contains twelve separate tank compartments 25. In some embodiments, a PGI controller 125 may be mounted to each hose adaptor assembly 35 and may be used to indicate the transported liquid type of the liquid product that is stored in the tank compartment 25. For example, the PGI controller 125 receives the transported liquid type of the liquid product stored in the tank compartment 25 from either the system controller 70 or the OFS 130 and displays the liquid product type. The display of information may be done on the display 80 and/or a PGI display 140 (shown in FIG. 11A). In another embodiment, an operator may input a loaded liquid type of liquid product that is being stored in the tank compartment 25 directly into the PGI controller 125 when the tank compartment 25 is filled at the loading station. The PGI controller 125 may display the loaded liquid type. The display of information may be done on the display 80 and/or a PGI display 140 (shown in FIG. 11A). In embodiments where the product transport vehicle 15 is used to store liquid petroleum products, the type of liquid product may be, for example gasoline, diesel, kerosene, etc. However, it should be understood that other types of liquid products may be stored in the tank compartments 25 and the PGI controller 125 and/or the system controller 70 may be used in a similar manner to identify those liquid products.

Referring again to FIG. 9, in embodiments, the hose adaptor assembly 35 for each tank compartment 25 may be fluidly coupled to a distribution tank 65 with a tank delivery connector 60 and a delivery hose 55. The tank delivery connector 60 may be an elbow coupler, a straight coupler, or a flexible coupler. An example of a suitable tank delivery connector 60 is the product delivery elbow, model number 60TT, 65TT, or 70TT by Civacon. However, it should be understood that alternative tank delivery connectors may be used. In embodiments where a tank delivery connector 60 is used to fluidly couple the hose adaptor assembly 35 to a distribution tank 65, the tank tag reader 95 may be located on the tank delivery connector 60 and positioned to read a corresponding tank tag 110 located on the distribution tank 65 when the tank delivery connector 60 is coupled to the distribution tank 65.

While FIG. 9 schematically depicts the use of a tank delivery connector 60 to couple the hose adaptor assembly 35 to the distribution tank 65, it should be understood that, in some embodiments, the tank delivery connector 60 may be omitted, such as when the hose adaptor assembly 35 is directly coupled to a distribution tank 65 with a delivery hose. In these embodiments, the tank tag reader 95 may be located on one end of the delivery hose and positioned to read a corresponding tank tag 110 located on the distribution tank 65 when the delivery hose is coupled to the distribution tank 65.

In some embodiments, the system controller 70 and associated components may be configured to determine that a valve corresponding to a tank compartment 25 to be unloaded is fluidly connected to a corresponding tank delivery connector 60 attached to a distribution tank 65 to prevent product spills. In some embodiments, the system controller 70 may also confirm that the same delivery hose 55 is fluidly coupled between the valve and the tank delivery connector 60 utilizing a set of RFID tags and a plurality of tag readers.

The system controller 70 may be communicatively coupled to an adaptor tag reader 85 and a hose tag reader 90. The adaptor tag reader 85 may be positioned on the hose adaptor 133 or a valve, e.g. the control valve 45. The hose tag reader 90 may be positioned on the tank delivery connector 60 in a location adjacent to the coupling point of a delivery hose 55 and opposite the tank tag reader 95. The delivery hose 55 may have a lock tag 100 at a lock end 102 of the delivery hose 55 and a connector hose tag 105 at a connector end 103 of the delivery hose 55. Both the lock tag 100 and the connector hose tag 105 may have the same hose ID information encoded on them, e.g. a first hose ID, a second hose ID, etc.

When the delivery hose 55 is coupled to the hose adaptor 133, the adaptor tag reader 85 interrogates the lock tag 100 and transmits the identification information (e.g. the first hose ID) to the system controller 70. When the delivery hose 55 is coupled to the tank delivery connector 60, the hose tag reader 90 interrogates the connector hose tag 105 and transmits the identification information (e.g. the first hose ID) to the system controller 70.

Referring to FIGS. 15 and 16, a front view and a side view of the control valve 45 is depicted. The control valve 45 and the hose adaptor 133 may be a single assembly as shown. The adaptor tag reader 85 may be coupled to a tag mount 800 and positioned on the hose adaptor 133 as shown or on the control valve body 810. In some embodiments, the OFS 130 may also be coupled to the control valve body 810 as shown. A control valve lever 815 is coupled to the control valve 45 and used by the operator to manually (e.g. physically) transition the control valve 45 from the normally locked state to the unlocked state. A pneumatic lock 820 may be coupled to the control valve body 810 and pneumatically coupled to the solenoid valve assembly of the PGI controller and/or the system controller. The pneumatic lock 820, when enabled by the PGI controller and/or the system controller 70, allows the control valve 45 to be transition from the normally locked state to the unlocked state and thereby open the control valve 45. The pneumatic lock 820 is coupled to the control valve lever 815 internal to the control valve body 810 and mechanically restricts (i.e. stops) the movement of the control valve 45 in the normally locked state.

In one embodiment, the system controller 70 verifies that a delivery hose 55 is coupled to each of the tank delivery connector 60 and the hose adaptor 133 and/or control valve 45. For example, when the delivery hose 55 is properly coupled to the tank delivery connector 60, the hose tag reader 90 is positioned to read the connector hose tag 105 and transmit a hose signal indicative of the hose ID to the system controller 70. In this embodiment, receipt of the hose signal indicative of the hose ID by the system controller 70 is sufficient to confirm that the delivery hose 55 is properly coupled to the tank delivery connector 60. Similarly, when the delivery hose 55 is properly coupled to the hose adaptor 133 or the control valve 45, the adaptor tag reader 85 is positioned to read the lock tag 100 and transmit a hose signal indicative of the hose ID to the system controller 70. In this embodiment, receipt of the hose signal indicative of the hose ID by the system controller 70 is sufficient to confirm that the hose is properly coupled to the hose adaptor 133 or the control valve 45. When the system controller 70 confirms that the delivery hose 55 is properly coupled to both the tank delivery connector 60 and the hose adaptor 133 or control valve 45, the system controller 70 may allow the corresponding control valve 45 to transition from the normally locked state to the unlocked state, subject to a determination that the transported liquid product type in the corresponding compartment matches the stored liquid product type of the distribution tank 65.

In another embodiment, the system controller 70 may confirm that a specific tank compartment 25 is fluidly coupled to a specific distribution tank 65 by matching the identification information of the lock tag 100 and the connector hose tag 105 and verifying the delivery hose 55 fluidly connects the specific control valve 45 or hose adaptor 133 to the correct tank delivery connector 60.

For example, the adaptor tag reader 85 may transmit the hose ID information to the system controller 70 using a bus or similar wiring method. In another embodiment, the adaptor tag reader 85 may transmit the hose ID information to the system controller 70 using a wireless connection, such as the wireless protocol and devices described herein. The hose tag reader 90 transmits the hose ID information to the system controller 70 using a wireless connection, such as the wireless protocol and devices as described above.

The tank tag reader 95 may further transmit a tank delivery connector ID signal to the system controller 70 indicative of an identity of the tank delivery connector 60. The tank delivery connector ID signal may be used to pair the tank delivery connector 60 to the system controller 70 associated with the product transport vehicle 15. For example, referring to FIG. 13, the system controller 70 may be paired with a first tank delivery connector 60a having a first tank delivery connector ID and a second tank delivery connector 60b having a second tank delivery ID. The pairing of the first tank delivery connector 60a and the second tank delivery connector 60b may ensure that the system controller 70 is not processing any information relating to a non-paired tank delivery connector 60 at the same distribution station 20.

When the system controller confirms that the delivery hose 55 is properly coupled to both the tank delivery connector 60 and the hose adaptor 133 or control valve 45 based on the received hose ID information, the system controller 70 may allow the corresponding control valve 45 to transition from the normally locked state to the unlocked state, subject to a determination that the transported liquid type of the liquid product in the corresponding tank compartment 25 matches the stored liquid product type of the distribution tank 65.

In another embodiment, the crossover protection system 10 configuration may be such that the delivery hose 55 may not have a lock tag 100 attached to the lock end 102 or connector hose tag 105 attached to the connector end 103 of the delivery hose 55 as described above. The tank tag reader 95 may read the tank tag 110 and transmit the tank tag's encoded liquid product type information directly to the system controller 70. The system controller 70 may allow or not allow the liquid product transfer based on the liquid product type information from the tank tag 110 without the need to verify the identity of the delivery hose 55. In this embodiment, the system controller 70 may enable only those valves that correspond to those tank compartments 25 that have a matching transported liquid type to transition from the normally locked state to the unlocked state. The system controller 70 may not act upon, or receive any other stored liquid type signals from other tank tag readers until one of the valves that has been enabled is transitioned to the unlocked state. The system controller 70, by only allowing a single tank compartment 25 to be unloaded at a time, can determine that the tank delivery connector 60 attached to the distribution tank 65 and is fluidly coupled to the matching tank compartment 25.

Figure 13:
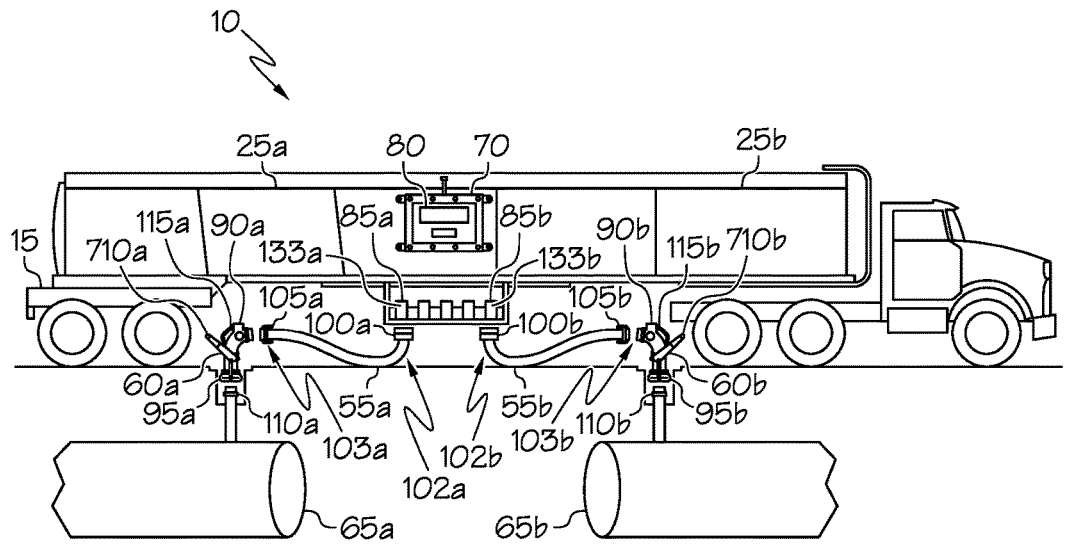
FIG. 13 schematically depicts the product transport vehicle at the distribution station according to one or more embodiments shown and described herein.
Figure 14:
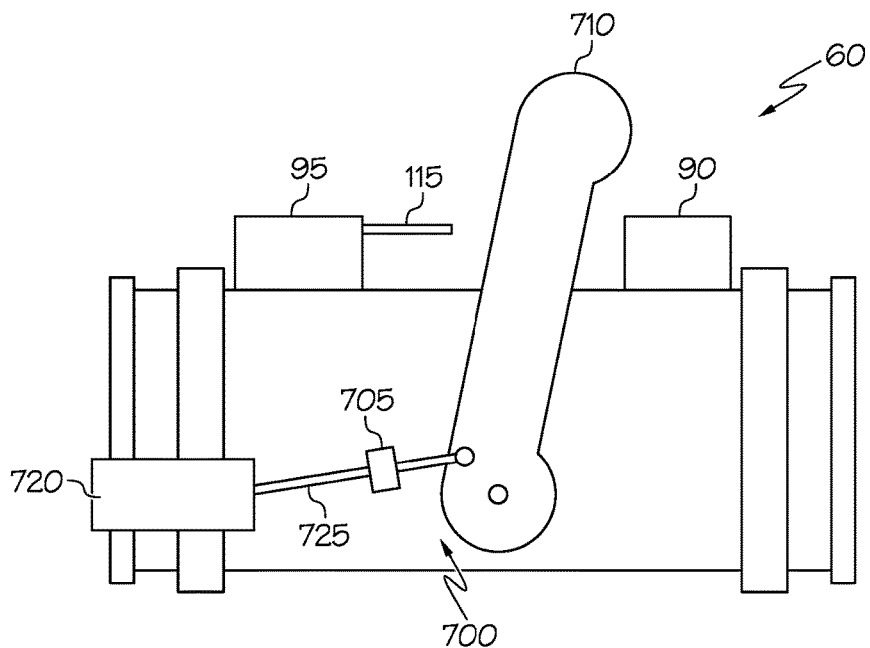
FIG. 14 is a side view of a tank delivery connector according to one or more embodiments shown and described herein.

Referring now to FIGS. 9, 13, and 14, in another embodiment, the tank delivery connector 60 may include a lock mechanism 700 coupled to the tank delivery connector 60, a power supply (not shown), and a lock sensor 705. The lock mechanism 700 may include a locking lever 710 with a locked position and an unlocked position coupled to a locking clamp 720. The locking lever 710, when in the unlocked position, maneuvers the locking clamp 720, via a lock shaft 725, to allow the coupling of the tank delivery connector 60 to the distribution tank 65. In the locked position, the locking lever 710 maneuvers the locking clamp 720, via the lock shaft 725, to compress a coupler (not shown) on the distribution tank to the tank delivery connector 60. In the locked position, the lock mechanism 700 mechanically secures the tank delivery connector 60 to a corresponding distribution tank 65. The power supply is coupled to the tank delivery connector and provides power for the tank tag reader 95; the hose tag reader 90 and/or the lock sensor 705. The lock sensor 705 is mechanically coupled to the lock mechanism 700 and electrically coupled to the tank tag reader 95 and may be a magnetic sensor, contact sensor, optical sensor, or the like. In one embodiment, the lock sensor 705 is a proximity sensor which senses whether the locking lever 710 is in the locked position and/or the unlocked position based on the locking lever's 710 position relative to the lock sensor 705. For example, the lock sensor 705 may provide the tank tag reader 95 with a delivery connector locked signal when the locking lever 710 is in the locked position. The tank tag reader 95 transmits the delivery connector locked signal to the system controller 70 when the tank delivery connector 60 is secured to the distribution tank 65. In one embodiment, power to the tank tag reader 95 may only be provided when the locking lever 710 is in the locked position as indicated by the lock sensor 705. The system controller 70 will not receive the tank tag signal until the tank delivery connector 60 is coupled to the distribution tank 65 and the locking lever 710 is in the locked position.

In yet another embodiment, the tank delivery connector 60 may include the lock mechanism 700 for locking the tank delivery connector 60 to the distribution tank 65, the power supply, and a switch (not shown). The switch may be mechanically coupled to the lock mechanism 700 and electrically coupled to the power supply and the tank tag reader 95. When the switch is actuated (e.g. pressed or toggled), the tank tag reader 95 will interrogate the tank tag 110 and transmit the stored liquid type signal to the system controller 70. In some embodiments, the switch may be positioned such that transitioning the locking lever 710 of the lock mechanism 700 from the unlocked state to the locked state may toggle the switch. In these embodiments, the switch may be used to "wake-up" the tank tag reader 95 which then automatically reads the tank tag 110 and transmits the stored fluid type signal to the system controller 70.

As described herein, the system controller 70 may use tags to prevent the mixing of dissimilar liquid products during loading and unloading of the liquid product and to verify coupling between the tank compartments of the product transport vehicle and a distribution tank. The adaptor tag reader 85, hose tag reader 90, and tank tag reader 95 (tag readers) shown in FIG. 9 may interrogate the lock tag 100, connector hose tag 105, and the tank tag 110 (tags) during operation of the crossover protection system 10. These tag readers may use optical interrogation, radio frequency interrogation, and/or physical interrogation to read the information encoded on the tags. For example, the tag readers may use an optical device, such as an image sensor, to take an image of the tag and decode the information contained on the tag. The tag reader may also be a laser scanner and/or bar code reader used to read the tag which may include a barcode or equivalent indicia. Alternatively, the tag readers include tactile input devices such as keypads or the like such that a product ID number found on the tag may be input into the tag reader by an operator. In the embodiments described herein, the tag readers are Radio Frequency Identification Device (RFID) tag reader and the tags are RFID tags. In embodiments, the tags may be passive RFID tags where the tag does not allow a read/write capability to occur within a tag memory.

In yet another embodiment, the system configuration may be such that the tags may be active RFID tags. The active RFID tag may allow the tag readers to read the tag's encoded information and write or overwrite information on the tags. For example, the liquid product type information may need to be changed to correspond to a change in type of liquid product being stored in the distribution tank 65. Or additional information may need to be included to the encoded information such as, for example, a timestamp of the last fill, the delivery vehicle ID number, the delivery company name, and/or batch number of the liquid product, etc.

Figure 12:
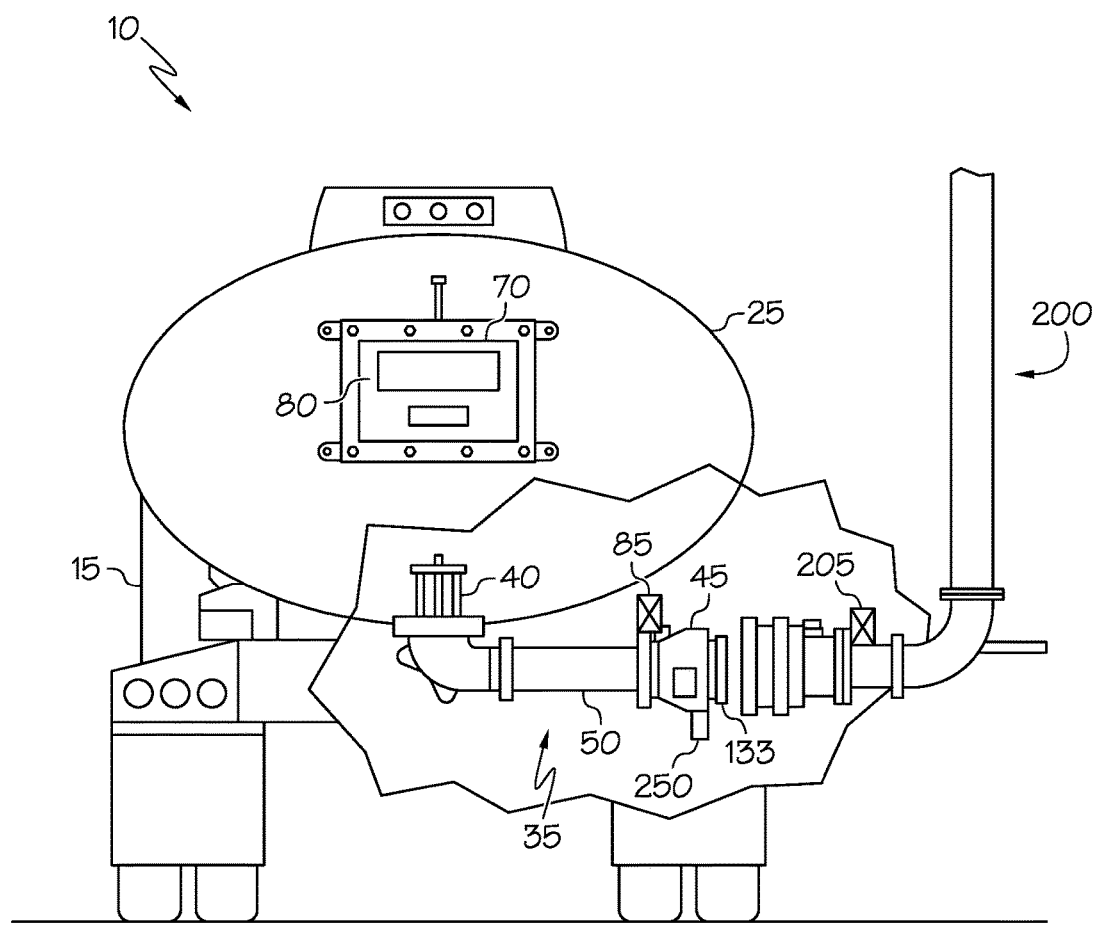
FIG. 12 schematically depicts the product transport vehicle at a loading station according to one or more embodiments shown and described herein.

Referring to FIG. 12, in some embodiments, the system controller 70 may further include a loading arm sensor 250. The loading arm sensor 250 may be mounted on the hose adaptor assembly 35 or the hose adaptor 133 and provides a loading arm signal to the PGI controller 125 and/or system controller 70 to determine when the loading arm 200, is fluidly coupled to the hose adaptor assembly 35 or hose adaptor 133. If the loading arm sensor 250 indicates that the loading arm 200 is not coupled to an hose adaptor assembly 35, the PGI controller 125 indicates on the PGI display 140 and/or the display 80 that the delivery hose 55 is not coupled to any of the storage compartments of the product transport vehicle 15 and the system controller 70 maintains the valve in the normally locked state to prevent a spill.

The operation of the crossover protection system 10 during loading and unloading of the product transport vehicle will now be described in more detail with specific reference to the Figures.

Referring now to FIG. 12, a product transport vehicle 15 is schematically depicted at a loading station. In some embodiments, the product transport vehicle 15 may arrive at the loading station completely empty. In the "empty" state, the PGI controller 125 and/or the system controller 70 may have the loaded liquid type in a particular tank compartment set either by the operator using the plurality of input devices 145 or by the OFS 130, which may indicate that a fluid is not present in chamber 306 (FIG. 2) of the sensor housing 304 (FIG. 2) indicating no liquid product in the tank compartment 25 or transfer pipe, or the pressure sensor 135 indicating the amount of liquid product is zero or near zero. In the later cases, the loaded liquid type may be set to "empty" when there is no liquid product in a particular tank compartment In some other embodiments, the product transport vehicle 15 may arrive at the loading station with at least one of the plurality of tank compartments 25 empty, as for example if the product transport vehicle 15 just returned from a product delivery run. The PGI controller 125 associated with that tank compartment 25 will indicate the last status from the product delivery run. For example, if the tank compartment 25 is empty, the PGI display 140 may indicate "empty" automatically based on readings from either the pressure sensor 135 or the OFS 130 and without input from the operator. Otherwise, the PGI display 140 will display an error code alternating message between "Prior Product Grade", "Retained Product", and "Frustrated Load" to indicate the tank compartment 25 is not empty from the product delivery run. The error code messages are related and may only scroll due to the limitations of the PGI display 140. The "Prior Product Grade" message indicates what product was in the tank compartment 25. The "Retained Product" message indicates that there is product left in the tank compartment 25, and the "Frustrated Load" message indicates that not all of the product was delivered to the distribution tank 65. To alert the operator to make a selection before filling the tank compartments 25, an alerting device associated with the PGI controller may be used. Examples of suitable alerting devices include, without limitation, an audible alert produced by an audio device 160, a flashing message or color from the PGI display 140, and/or a visual device, such as one or more LEDs (not shown). The alerting device may be associated with a specific PGI controller 125 allowing the operator to easily locate which PGI controller 125 needs attention. If the PGI controller 125 is not used on the product transport vehicle 15, the system controller 70 may indicate the status of individual tank compartments 25 of the plurality of tank compartments using the above convention, the display 80, and an alerting device associated with the system controller 70.

Referring to FIGS. 10, 11A, 11B, and 12, to load liquid product into the tank compartment 25, a loading arm 200 is connected to the hose adaptor 133 of the hose adaptor assembly 35 to fill the corresponding tank compartment 25. The loading arm 200 is fluidly coupled to a storage tank (not shown) of the loading station. In one embodiment, the PGI controller 125 may not allow the operator to load the liquid product into one or more of the tank compartments 25 until the loaded liquid type is selected as discussed above. The PGI controller 125 may receive a valve open air signal from an air selector valve panel (not shown) indicating the operator has tried to open an individual valve of the plurality of valves. The PGI controller 125 and/or the system controller 70 may display an error message and instruct the operator that the loaded liquid type is not selected or that a mismatch of liquid types may occur between the liquid product the operator wishes to load and a current transported liquid type already present in the tank compartment 25. The PGI controller 125 and/or system controller may maintain the corresponding valve in the normally locked state until the PGI controller 125 and/or the system controller 70 indicate that the loaded liquid type has been entered and/or the loaded liquid type and the transported liquid type are the same. Once the loaded liquid type is accepted by the PGI controller 125 and/or system controller 70, the PGI controller and/or system controller 70 may enable the corresponding valve to transition from the normally locked state to the unlocked state and the operator may then manually transition the valve to open and fill the tank compartment 25 with the liquid product.

In embodiments, the PGI controller 125 and/or the system controller 70 may be communicatively coupled to the braking system of the product transport vehicle 15, either pneumatically or electrically, as described above. In these embodiments, the system controller 70 may require a brake signal to indicate that the parking brake on the product transport vehicle 15 is released before loading or unloading of the liquid product may be allowed to proceed. The PGI controller 125 and/or the system controller 70 may be coupled to the parking brake sensor 79 which provides the brake signal. The brake signal is indicative of whether the brake is engaged or released. In other embodiments, the system controller 70 may use multiple indicators to determine the product transport vehicle's current mode of operation (i.e. loading or unloading product). These indicators may include, for example, the brake signal, the pressure sensor signals, and communications with the OFS 130. In a similar manner, the system controller 70 may utilize the accelerometer signal from the accelerometer 78 to determine if the product transport vehicle 15 is moving before allowing any of the plurality of valves to transition from the normally locked state to the unlocked state and allow product loading/unloading to occur. For example, if the accelerometer 78 indicates that the product transport vehicle is moving, the system controller 70 may prevent the emergency valve 40 and/or the control valve 45 from being transitioned from the normally locked state to the unlocked state. Likewise, once the accelerometer 78 indicates that the transport vehicle has begun moving, the PGI controller 125 and/or the system controller 70 may transition the valve from the unlocked state to the normally locked state to cease any loading or unloading of product from or to the tank compartment 25 and indicate that the current operating mode has concluded.

In one embodiment, as the tank compartment 25 is filled, the OFS 130 determines the transported liquid type of the liquid product, as described previously herein. The PGI controller 125 and/or the system controller 70 may read or poll the OFS 130 to receive the transported liquid type determined for the liquid product by the OFS 130. In one or more embodiments, the identity of the liquid product is stored in the computer-readable medium of the PGI controller and/or the system controller 70 and indexed according to the associated tank compartment 25 such that the contents of each tank compartment are recorded in the computer-readable medium. In some other embodiments, the OFS 130 is utilized to continuously or periodically monitor and determine the fluid type of the liquid stored in the tank compartment 25 and continuously or periodically provide the system controller 70 with the transported liquid type.

If, for example, the system controller 70 determines that the transported liquid type from the OFS 130 does not match the loaded liquid type indicated by the operator through the PGI controller 125, the system controller 70 and/or the PGI controller 125 will either maintain the valve in the normally locked state or transition the valve from the unlocked state to the normally locked state, thereby closing the valve and stopping the flow of liquid product into the tank compartment 25. The operator may override the system controller 70 to manually transition the valve from the normally locked state to the unlocked state and continue filling the tank compartment 25.

In another embodiment, the system controller 70 or the PGI controller 125 may mimic an error indicator of an existing control system on the product transport vehicle 15 to stop the flow of liquid product into the tank compartment 25 when the system controller 70 determines that the transported liquid type from the OFS 130 does not matches the loaded liquid type indicated by the operator. For example, the system controller 70 or the PGI controller 125 may stop the flow of liquid product from the storage tank to the tank compartment 25 by mimicking an overfill condition in the tank compartment to the onboard overfill detection system (not shown). The overfill condition may be communicated to the onboard overfill detection system coupled to the tank compartment 25 via an overfill condition signal. The onboard overfill detection system monitors for an overfill condition in the individual tank compartments 25 of the product transport vehicle 15 using a point level sensor (not shown). The point level sensor may be positioned in the tank compartment and transmit a point signal to the system controller 70 to indicate whether there is an overfill condition of liquid product within the tank compartment 25.

The onboard overfill detection system on the product transport vehicle 15 is communicatively coupled to a loading station control system (not shown) in the loading station. The loading station control system controls the flow of liquid product from the storage tanks. When the system controller 70 or the PGI controller 125 determines that the transported liquid type from the OFS 130 does not match the loaded liquid type indicated by the operator, the overfill condition signal may be transmitted to the onboard overfill detection system. The onboard overfill detection system will instruct the loading station control system to cease loading liquid product onto the tank compartment 25 on the product transport vehicle.

In another embodiment, the system controller 70 and/or PGI controller 125 may receive a valve open signal indicating the operator has opened the emergency valve 40 and/or the control valve 45 to allow the loading of liquid product into the tank compartment 25. The PGI controller 125 and/or the system controller 70 may then start to poll the OFS 130 to determine the transported liquid type of the liquid product. The identity (i.e., transported liquid type) of the liquid product is stored in the computer-readable medium of the PGI controller and/or the system controller 70 and indexed according to the associated tank compartment 25 such that the contents of each tank are recorded in a computer-readable medium.

Where the liquid product is a petroleum product, the PGI controller 125 and/or system controller 70 determine whether the liquid product in the tank compartment 25 is a distillate or gasoline liquid product based on the transported liquid type received from the OFS 130. When the transported liquid type indicates that the liquid product is gasoline, the PGI controller 125 and/or system controller 70 may alert the operator to enter in the product grade (i.e., the octane rating) of the gasoline that has been loaded into the tank compartment 25 by flashing "Set Grade" on the PGI display. In this embodiment, the operator may select from a variety of pre-programmed options to set the grade of the liquid product being loaded. The PGI controller 125 elec-trically communicates a signal encoding the selection to the system controller 70. The system controller 70 stores, in a computer readable medium, the liquid product type information for the tank compartment 25 holding the liquid product. The system controller 70 may poll the OFS 130 to receive the transported liquid type determined by OFS 130 continuously or at periodic intervals during transfer of the material. The system controller 70 may compare the transported liquid type received from the OFS 130 to the liquid product type and grade entered by the operator. The process is repeated as other tank compartments 25 are filled in the product transport vehicle 15 with either the same liquid product or a different liquid product.

Still referring to FIG. 12, in one embodiment, the loading arm 200 may include a loading arm tag 205 having the loaded liquid type encoded therein. The adaptor tag reader 85 may interrogate the loading arm tag 205 and transmit a first signal encoding a loaded liquid type to the system controller 70. The loaded liquid type information is received by the wireless module and recorded to a computer readable medium of the system controller 70. The loaded liquid type information is correlated to the tank compartment 25 that the liquid product is being loaded into. As the liquid product is being loaded into the tank compartment 25, the OFS 130 determines the transported liquid type and communicates a transported liquid type to the system controller 70, as described above. Once the system controller 70 has determined the identity of the liquid product being loaded, the system controller 70 may either send a signal to the PGI controller 125 indicative of the transported liquid type as determined by the OFS 130 for indication on the PGI display 140 and/or make the determination of the transported liquid type matches the loaded liquid type. In this embodiment, the loaded liquid type may either be derived from the loading arm tag 205 or from operator input into the PGI controller 125. For example, when the liquid product is a liquid petroleum product, the PGI display 140 may display either "Distillate Detected" or "Gasoline Detected.".

Where gasoline is detected, the PGI controller 125 may prompt the user to "Set Grade", as noted above. In this embodiment, the operator may select from a variety of pre-programmed options to set the grade of the liquid product being loaded. The PGI controller 125 then communicates a grade signal encoding a grade selection to the system controller 70. The system controller 70 compares the grade selection to the loading arm tag 205 loaded liquid type and to the transported liquid type received from the OFS 130 to confirm a match. The system controller 70 stores, in a computer readable medium, the transported liquid type for the tank compartment 25 holding the liquid product based on either the loaded liquid type or the transported liquid type determined by the OFS 130. The process is repeated as other tank compartments 25 are filled in the product transport vehicle 15 with either the same liquid product or a different liquid product.

If the liquid product information from the tags does not match the transported liquid type determined by the OFS 130 or does not match the loaded liquid type from the operator's input, the system controller 70 may disable the transition of the valve from the normally locked state to the unlocked state to prevent the flow of liquid product into the tank compartment 25. The PGI controller 125 may also indicate an error on the PGI display 140 when a match is not made to warn the operator or the system controller 70 may indicate the error on the display 80. The indication may be an audible signal, visual display, etc. as described below. In embodiments, the operator may override the system controller 70 to enable the transition of the valve from the normally locked state to the unlocked state and continue filling the tank compartment 25.

FIG. 13 schematically depicts the product transport vehicle 15 at a distribution facility unloading liquid product into a first distribution tank 65*a* and a second distribution tank 65*b* from a first tank compartment 25*a* and a second tank compartment 25*b*, respectively. The operator initially chooses which tank compartment (e.g. the first tank compartment 25*a* or the second tank compartment 25*b*) from which the first distribution tank 65*a* and the second distribution tank 65*b* will be filled. If the first tank compartment 25*a* is chosen to fill the first distribution tank 65*a*, the operator may fluidly couple a first delivery hose 55*a* to a first hose adaptor 133*a* corresponding to the first tank compartment 25*a*. The operator then fluidly couples a first tank delivery connector 60*a* to the first delivery hose 55*a* and fluidly couples the first tank delivery connector 60*a* to the first distribution tank 65*a*. The operator may repeat similar steps to fill the second distribution tank 65*b* from the second tank compartment 25*b* with either the same liquid product type or a different liquid product type.

In some embodiments, the system controller 70 may confirm that each delivery hose 55 is properly connected to the distribution tank and a tank compartment, as described hereinabove. In these embodiments, the system controller 70 prevents the discharge or unloading of product from any tank compartment until at least one connection is confirmed. This is accomplished by maintaining all the valves coupled to the tank compartments in a normally locked state until the connections are confirmed.

The first tank compartment 25*a* is now fluidly connected to the first hose adaptor 133*a*, the first delivery hose 55*a*, the first tank delivery connector 60*a*, and the first distribution tank 65*a*. Similarly, the second tank compartment 25*b* is now fluidly connected to the second hose adaptor 133*b*, the second delivery hose 55*b*, the second tank delivery connector 60*b*, and the second distribution tank 65*b*. The system controller 70 then confirms that the fluid connections will not cross-contaminate the liquid products stored in the respective distribution tanks 65*a*, 65*b*.

In one embodiment, the process of product verification begins when the tank delivery connectors 60*a*, 60*b* are locked on to the corresponding distribution tank 65*a*, 65*b*. For example, in one embodiment, the tank delivery connectors 60*a*, 60*b* may include a locking lever and a lock sensor, as described above, and power to the tank tag reader 95 is only provided when the locking lever is in the locked position. Once the first locking lever 710*a* is in the locked position, the first tank tag reader 95*a* interrogates a first tank tag 110*a* to retrieve the liquid product type, and other information encoded on the first tank tag 110*a*. Alternatively, the operator may manually actuate a switch on the first tank delivery connector 60*a* to manually wake-up a first tank tag reader 95*a*. Once the first tank tag reader 95*a* is powered on, the first tank tag reader 95*a* interrogates the first tank tag 110*a* and transmits a stored liquid type signal indicative of the stored liquid type to the system controller 70. The first tank tag reader 95*a* may use a first tank connector antenna 115*a* to transmit the stored liquid type signal to the system controller 70.

The system controller 70 may be configured to communicated with a limited number of tank tag readers. For example, the first tank tag reader 95*a* and the second tank tag reader 95*b* may be registered with the system controller 70. The registration of one or more tank tag readers to the system controller may eliminate any cross-talk with other tank tag readers from other product delivery trucks at the same distribution station 20.

The system controller 70 receives the stored liquid product type signal from the first tank delivery connector 60*a* and stores it in the computer-readable medium. The system controller 70 may then compare the stored liquid type to the transported liquid type contained in any of the tank compartments of the product transport vehicle to determine if a match is present. If the system controller 70 determines that any tank compartment contains a transported liquid type matching that of the stored liquid type, the system controller 70 transitions the corresponding valve of that tank compartment from the normally locked state to the unlocked state, thereby allowing liquid product to be released from the corresponding tank compartment. However, if the system controller 70 determines that a tank compartment does not contain a transported liquid type matching that of the stored liquid type, the system controller 70 maintains the corresponding valve of that tank compartment in the normally locked state, thereby preventing the release of liquid product from the tank compartment.

Once the system controller 70 has determined that at least one tank compartment contains a transported liquid type that matches the stored liquid type and transitioned the corresponding valve to an unlocked state, the operator may operate the air selector valve for that tank compartment (in this example, the first tank compartment 25*a*) from an air selector valve panel (not shown) to manually (e.g. physically) open the valve and allow the flow of the liquid product from the first tank compartment 25*a*.

In some embodiments, the system controller 70 may require the first PGI controller 125*a* and/or the system controller 70 to receive a valve open air signal from an air selector valve panel (not shown) indicating the operator has opened the valve to release the product from the first tank compartment 25*a*. In this embodiment, the system controller 70 may prevent any other valves corresponding to any other tank compartments from being opened until the valve from the first tank compartment 25*a* has been physically closed after being opened (although it should be understood that the valve may remain in either the unlocked state or be transitioned to the normally unlocked state). Once the valve corresponding to the first tank compartment 25*a* has been physically closed, the system controller 70 may allow the operator to repeat similar steps to fill the second distribution tank 65*b* from the second tank compartment 25*b* with either the same liquid product type or a different liquid product type.

In some embodiments, if the system controller 70 detects a liquid product mismatch during one or more of the above connection sequences, it may provide the operator with a visual and/or audible warning. For example, in some embodiments the system controller 70 may instruct the first PGI controller 125*a* or the second PGI controller 125*b* to display a warning to the operator. In some embodiments, the first PGI controller 125*a* and/or the second PGI controller 125*b* may provide an audible alert produced by an alerting device, a flashing message or color from the PGI display, and/or a visual device, such as one or more LEDs, to notify the operator of the liquid product mismatch. In another embodiment, the system controller 70 may alert the operator if a mismatch is determined. The system controller 70 may alert the operator via the display 80, an audible alert produced by an alerting device, a flashing message or color from the display 80, and/or a visual device, such as one or more LEDs, to notify the operator of the liquid product mismatch.

Referring to FIGS. 9, 10, and 13, in one embodiment, the OFS 130 may be positioned in the pipe connection 50, as described above. When, the pipe connection 50 is dry, such as when there is no liquid in either the pipe connection 50 or the corresponding tank compartment 25 after the tank compartment 25 was initially loaded through the manlid 30, the OFS 130 may determine that a fluid is not present in the chamber 306 (FIG. 2) of the sensor housing 304 (FIG. 2), which may indicate that the pipe connection 50 is dry (i.e., no liquid product is present in the tank compartment 25 or the pipe connection 50). As previously described, the OFS 130 may generate the "no liquid present" message and may transmit, or alternately the system controller 70 may read, the "no liquid present" message, which may be indicative of an empty pipe condition. Upon receipt of this message, the PGI controller 125 and/or the system controller 70 indicates on the PGI display 140, or alternately the display 80, that the OFS 130 is not able to detect the presence of a liquid product in the tank compartment 25. For example, the fluid product type matching process may be initiated by waking-up the first tank tag reader 95a, as described above. The first tank tag reader 95a interrogates the first tank tag 110a to retrieve the stored liquid type indicative of the liquid product in the first distribution tank 65a and transmits the stored liquid type signal encoding the stored liquid type to the system controller 70. The system controller 70 then transitions the valves corresponding to each tank compartment to the unlocked state from the normally locked state. This condition allows the operator system controller to flood the pipe connection 50 with liquid product from the first tank compartment 25a by opening the emergency valve 40. The OFS 130 associated with the now flooded pipe connection 50 corresponding to the first tank compartment 25a determines the transported liquid type of the liquid product in each of the tank compartments and sends the transported liquid type for each of the compartments to the system controller 70. The system controller 70 compares the transported liquid type received from the OFS 130 to the stored liquid type in each of the distribution tanks 65a, 65b. For each tank compartment which contains a transported liquid type which matches the stored liquid type, the system controller transitions the control valve 45 corresponding to each tank compartment with the matching transported liquid type from a normally locked state to an unlocked state to allow the unloading of the liquid product from the compartment by the operator. For those tank compartments in which the transported liquid type and the stored liquid type do not match, the system controller 70 will maintain the corresponding control valve in the normally locked state to ensure that the liquid product from tank compartment is not unloaded and may also alert the operator to the mismatch.

In embodiments where the OFS 130 is positioned in the tank compartment, this procedure to flood the pipe connection 50 may not be needed.

As indicated above, in some embodiments the system controller 70 transitions the valves corresponding to each tank compartment from the normally locked state to the unlocked state by the operator when the tank compartment is determined to contain a transported liquid type which matches the stored liquid type in a distribution tank. The transition from the normally locked state to the unlocked state allows the operator to then control the unloading of the liquid product manually by opening or closing an air selector valve on an air selector valve panel. The air selector valve panel may be utilized to physically open or close a valve corresponding to a tank compartment which contains a transported liquid type product matching the stored liquid type of a distribution tank. In other words, liquid product from a particular tank compartment may not be unloaded from the tank compartment 25 if the system controller 70 has not transitioned a corresponding valve from a normally locked state to an unlocked state and the operator physically opens the valve utilizing the air selector.

Referring to FIGS. 9, 10, and 11A, if the OFS 130 transmits the "no fluid present" message to indicate that there is no fluid detected in the chamber 306 (FIG. 2) of the sensor housing 304 (FIG. 2) (i.e., there is no liquid product in the tank compartment 25), the PGI controller 125 will display an "empty" status. If the OFS 130 determines that a fluid is present in the chamber 306 of the sensor housing 304, which indicates that liquid product is in the tank compartment, the accelerometer 78 indicates the product transport vehicle 15 is in motion, and/or the parking brake is released, the PGI controller 125 may display a warning. For example, in one embodiment, the PGI controller 125 may display "Prior Product Grade" and "Retained Product" and "Frustrated Load" in alternating messages and prevent the valve of the plurality of valves corresponding to the tank compartment 25 from being opened and the product unloading and/or loading process from proceeding when the product transport vehicle is in motion and/or the parking brake is released.

The system controller 70 may display an "unloading" status in the display 80 as the liquid product is being unloaded from the tank compartment 25 into the distribution tank 65. The OFS 130 may monitor whether a fluid is present in the chamber 306 (FIG. 2) of the sensor housing 304 (FIG. 2) and may transmit to the system controller 70 a "fluid present" message to indicate a wet status or a "no fluid present" message to indicate a dry status. The system controller 70 may use the wet status and the dry status to update the computer-readable medium with information on whether any liquid product remains in the tank compartment 25 after unloading is complete.

Figure 17:
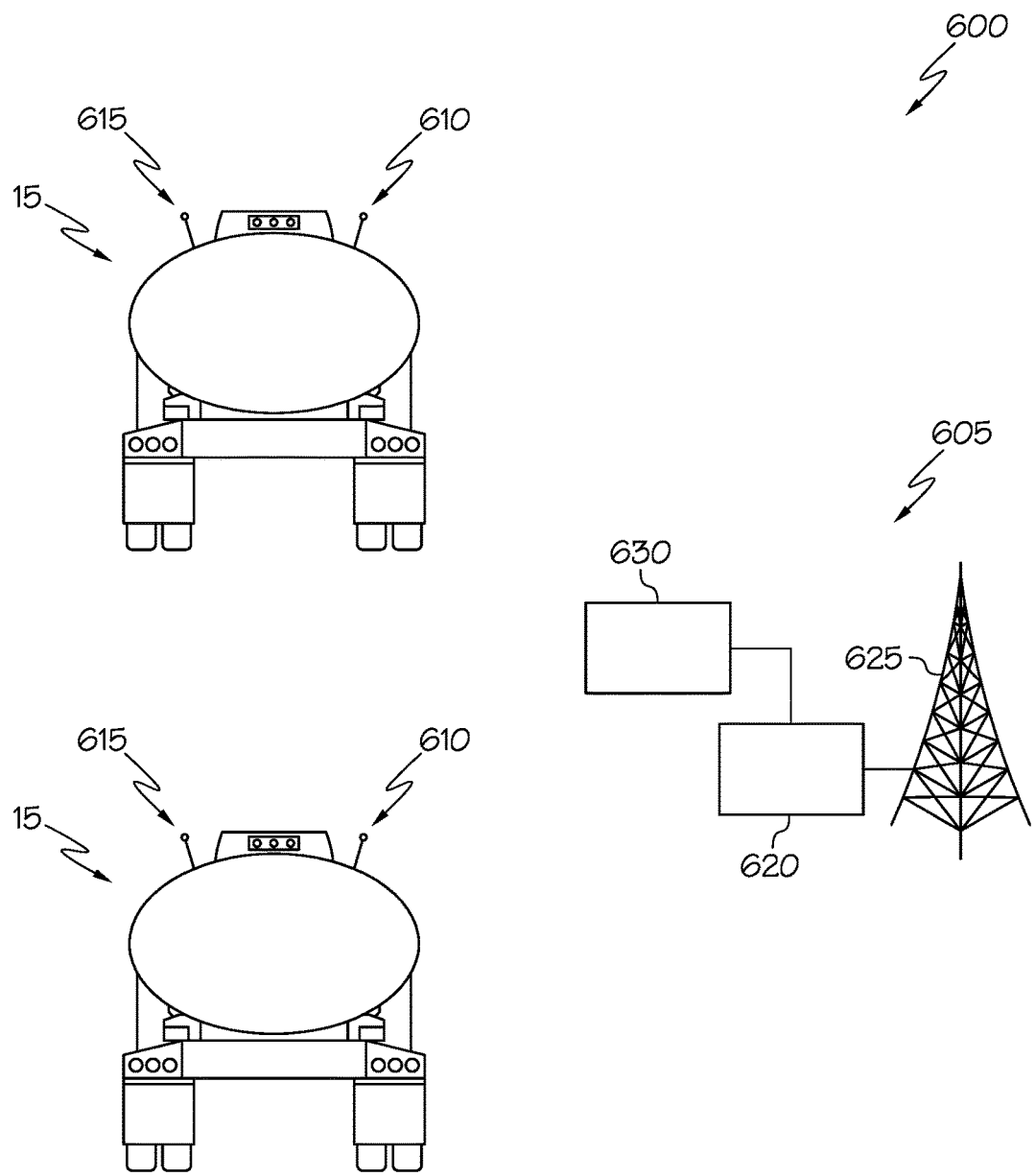
FIG. 17 schematically depicts a fleet management system according to one or more embodiments shown and described herein.

Referring now to FIG. 17, a fleet management system 600 is shown. The fleet management system 600 manages individual product transport vehicles 15 of a plurality of product transport vehicles as they travel about a geographic region. The size of the geographic region may depend on the ability of the individual product transport vehicles 15 to communicate with a base station 605. For example, a radio communication system may only provide a geographic region of about 50 miles, whereas a cellular communication system may have a geographic region that is nationwide. Further, a satellite communication system may allow for a geographic region that is worldwide.

Referring not to FIGS. 9 and 17, to communicate with the base station 605, the individual product transport vehicles 15 of the plurality of product transport vehicles may include a global position system (GPS) antenna 610 and a transmitter antenna 615 communicatively coupled to the system controller 70. The system controller 70 receives from the GPS antenna a location signal indicative of a current location of the individual product transport vehicles 15 of the plurality of product transport vehicles. The transmitter antenna 615 may be a radio antenna, a cellular antenna, a satellite antenna or any antenna that matches the communication protocol (radio, cellular, satellite, etc.) of the communication system between the individual product transport vehicles 15 of the plurality of product transport vehicles and the base station 605.

The system controller 70 may transmit, using the transmitter antenna 615, an ID signal indicative of the current location and a product transport vehicle ID to the base station 605 at regular intervals to allow a fleet system controller 620 to receive the ID signal and track the current location and product transport vehicle ID of the individual product transport vehicles 15 of the plurality of product transport vehicles. In another embodiment, the system controller 70 may transmit the ID signal only when the individual product transport vehicles 15 of the plurality of product transport vehicles is at a distribution station 20 and/or unloading a tank compartment 25.

The base station 605 may include a receiver antenna 625 coupled to the base station 605 and communicatively coupled to the transmitter antenna 615 on the individual product transport vehicles 15 of the plurality of product transport vehicles. The fleet system controller 620 may be communicatively coupled to the receiver antenna 625 and a fleet display 630. The fleet system controller 620 may include a processor and a storage medium containing computer readable and executable instructions which, when executed by the processor, cause the fleet system controller 620 to automatically: receive the current location of the individual product transport vehicles 15 of the plurality of product transport vehicles; receive the vehicle identification; and record the current location and the vehicle identification on the storage medium.

Still referring to FIGS. 9 and 17, the system controller 70 may have a LUT of stored locations of a plurality of distribution tank 65 locations, the individual distribution tank locations indicated by GPS coordinates. The LUT may also include the proper stored liquid type of the distribution tanks 65 at each stored location. In another embodiment, the system controller 70 may receive a stored location signal indicative of the stored location of the distribution tank 65. The stored location signal may originate with the base station 605 and be in response to receiving the ID signal with the individual product transport vehicles 15 current location. In both embodiments described above, the stored location may include the GPS coordinates of the distribution tank 65, a location liquid type indicative of the liquid product within the distribution tank 65, and other identifiable information, such as for example, the mailing address of the distribution station 20 in which the distribution tank 65 is located, contact information for the responsible party for the distribution tank 65, emergency contact information, and the like. The information indicated by the stored location may be displayed on the display 80 or the PGI display 140 (FIG. 11A) for the operator's use.

The system controller 70 may compare the current location indicated by the location signal from the GPS antenna 610 to the stored location GPS coordinates to determine which distribution tanks 65 are at the current location. From that determination, the system controller 70 may compare the location liquid type to either the stored liquid type transmitted by the tank tag reader 95 or the transported liquid type indicated by the OFS 130. From either of those comparisons, if they match, the system controller may either enable the transition of the valve of the plurality of valves corresponding to the tank compartment 25 to allow the unloading of the liquid product from the tank compartment 25 by the operator or transition the valve of the plurality of valves corresponding to the tank compartment 25 to the unlocked state from the normally locked state. If, either of those comparisons indicates a mis-match, the system controller 70 may disable the valve of the plurality of valves corresponding to the tank compartment 25 from transitioning from the normally locked state to the unlocked state.

The outcome of the comparisons described above between the stored liquid type (either from the tank tag or operator input), location liquid type, and the transported liquid type, may be transmitted to the base station 605 to be recorded on the computer readable medium by the fleet system controller 620. Specifically, the system controller 70 may transmit, using the transmitter antenna 615, a lock data signal indicative of lock data. The lock data may include the comparison results, the current state of individual valves of the plurality of valves, whether liquid product is or was unloaded, the amount of liquid product in each tank compartment 25, and whether the operator has override the system controller 70.

The physical location of the system controller 70 as shown in the FIGS. 9, 12, and 13 are for illustration purposes only, and the system controller 70 may be mounted in any location on the product transport vehicle 15. Furthermore, the product transport vehicle 15 may have more than one transportation tank and the product transport vehicle 15 may be a fuel truck, an aircraft, or a ship and/or boat.

The crossover protection system 10 provides an automatic check and/or intervention to prevent the mixing of dissimilar products at a distribution station 20. The crossover protection system 10 uses the OFS 130 to positively identify the fluid type of the liquid product to make a determination if the products match before allowing the products to mix in the distribution tank 65. Accordingly, human interaction or intervention to identify the product is not required.

The present disclosure may be embodied in hardware and/or in software (including firmware, resident software, micro-code, etc.). The system controller 70 may have at least one processor and the computer-readable medium. A computer-usable or the computer-readable medium or memory module may be any medium that can contain, store, communicate, propagate, or transport the program for use by or in connection with the instruction execution system, apparatus, or device.

The computer-usable or computer-readable medium or memory module may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Computer program code for carrying out operations of the present disclosure may be written in a high-level programming language, such as C or C++, for development convenience. In addition, computer program code for carrying out operations of the present disclosure may also be written in other programming languages, such as, but not limited to, interpreted languages. Some modules or routines may be written in assembly language or even micro-code to enhance performance and/or memory usage. However, software embodiments of the present disclosure do not depend on implementation with a particular programming language. It will be further appreciated that the functionality of any or all of the program modules may also be implemented using discrete hardware components, one or more application specific integrated circuits (ASICs), or a programmed digital signal processor or microcontroller.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. An optical fluid sensor comprising:
   a body defining a chamber and having one or more apertures to allow a fluid to enter the chamber;
   a light source optically coupled to the chamber and configured to emit IR, UV, and visible light into the chamber;
   a detector optically coupled to the chamber and configured to receive light from the chamber, wherein the detector measures an intensity of one or more wavelengths of light received by the detector, wherein the light source and the detector are positioned such that, when fluid is disposed within the chamber, emitted light from the light source passes into and through the fluid disposed in the chamber before being received by the detector;
   a processor;
   one or more memory modules communicatively coupled to the processor; and
   machine readable instructions stored in the one or more memory modules that cause the optical fluid sensor to perform at least the following when executed by the processor:
   transmit a control signal to the light source to cause the light source to emit IR light into the chamber;
   receive IR light at the detector;
   process the IR light received at the detector to determine an intensity of the received IR light;
   compare the intensity of the received IR light to a threshold intensity;
   determine that a fluid is present based on the comparison;
   transmit another control signal to the light source to cause the light source to emit UV light into the chamber in order to cause the fluid to fluoresce visible light;
   receive visible light at the detector;
   process the received visible light to determine wavelength and intensity information for the received light;
   compare the wavelength and intensity information for the received light to the one or more fluid profiles stored in the one or more memory modules, wherein each of the one or more fluid profiles comprises information on one or more fluorescent properties of the fluid; and
   determine a fluid type of the fluid in the chamber based on the comparison.

2. The optical fluid sensor of claim 1, further comprising a reflector.

3. The optical fluid sensor of claim 2, wherein the light source and the detector are positioned at a first side of the chamber and the reflector is positioned at a second side of the chamber, wherein when fluid is disposed within the chamber, the emitted light from the light source travels through the fluid in the chamber, reflects off of the reflector, and travels to the detector.

4. The optical fluid sensor of claim 1, wherein the light source and the detector are fluidly isolated from the fluid by a transparent member positioned between the light source and the chamber; wherein the transparent member allows light from the light source to pass through into the fluid.

5. The optical fluid sensor of claim 1, further comprising at least one temperature sensor to measure a temperature of the light source or a fluid temperature.

6. The optical fluid sensor of claim 1, further comprising machine readable instructions stored in the one or more memory modules that cause the optical fluid sensor to perform at least the following when executed by the processor:
   transmit a control signal to the light source to cause the light source to emit visible light into the chamber;
   receive visible light at the detector;
   process the received light to determine wavelength and intensity information for the received light;
   compare the wavelength and intensity information for the received light to one or more fluid profiles stored in the one or more memory modules; and
   determine a fluid type of the fluid in the chamber based on the comparison.

7. The optical fluid sensor of claim 1, further comprising machine readable instructions stored in the one or more memory modules that cause the optical fluid sensor to perform at least the following when executed by the processor:
   receive a temperature signal from a temperature sensor; and
   adjust one or more fluid profiles stored in the one or more memory modules or the wavelength and intensity information of the received light based on the temperature signal.

8. A crossover protection system comprising:
   a product transport vehicle comprising a tank compartment for containing a liquid product;
   a valve coupled to the tank compartment, the valve regulating a flow of liquid product from the tank compartment and having a normally locked state;
   the optical fluid sensor of claim 1 positioned to contact the liquid product stored in the tank compartment;
   a tank delivery connector fluidly coupled to a distribution side of the valve, the tank delivery connector comprising a tank tag reader for interrogating a tank tag coupled to a distribution tank separate from the product transport vehicle to retrieve a stored liquid type encoded on the tank tag, wherein the stored liquid type is indicative of a type of the liquid product in the distribution tank; and
   a system controller communicatively coupled to the valve, the optical fluid sensor, and the tank delivery connector, the system controller comprising a processor and one or more memory modules communicatively coupled to the processor.

9. The crossover protection system of claim 8, further comprising machine readable instructions stored in the one or more memory modules that cause the sensor to perform at least the following when executed by the processor:
   determine a transported liquid type based on an output from the optical fluid sensor;

receive the stored liquid type signal transmitted by the tank delivery connector;
determine the stored liquid type based on the stored liquid type signal;
compare the transported liquid type to the stored liquid type;
maintain the valve in the normally locked state when the stored liquid type and the transported liquid type do not match to prevent the flow of liquid product from the tank compartment; and
transition the valve from the normally locked state to an unlocked state when the stored liquid type and the transported liquid type match, thereby permitting the flow of liquid product from the tank compartment.

10. The optical fluid sensor of claim 1, further comprising a first temperature sensor operatively arranged within the chamber to measure a temperature of the fluid disposed in the chamber, and a second temperature sensor operatively arranged in the body to measure a temperature of the light source and the detector.

11. The optical fluid sensor of claim 1, wherein the light source emits each of the IR light, the visible light, and the UV light in a series.

12. An optical sensor system comprising:
a light source configured to emit IR, UV, and visible light into a fluid;
a detector configured to measure intensities of one or more wavelengths of IR light and visible light received by the detector;
a processor;
one or more memory modules communicatively coupled to the processor; and
machine readable instructions stored in the one or more memory modules that cause the optical sensor system to perform at least the following when executed by the processor:
transmit a control signal to the light source to cause the light source to emit the IR light into the fluid;
receive IR light at the detector in response to emitting the IR light into the fluid;
process the received IR light to determine an intensity of the IR light;
determine whether the fluid is present based on the intensity of the IR light received by the detector;
after determining whether the fluid is present, transmit a control signal to the light source to cause the light source to emit visible light into the fluid;
receive visible light at the detector in response to emitting the visible light into the fluid;
process the visible light received at the detector to determine wavelength and intensity information for the visible light received, wherein the visible light received represents the light transmitted through the fluid;
after processing the visible light received at the detector, transmit a control signal to the light source to cause the light source to emit UV light into the fluid to cause the fluid to fluoresce;
receive the visible light fluoresced by the fluid at the detector in response to emitting the UV light into the fluid;
process the visible light fluoresced by the fluid and received at the detector to determine wavelength and intensity information for the visible light fluoresced by the fluid;
compare the wavelength and intensity information for the received light transmitted through the fluid and the visible light fluoresced by the fluid to one or more fluid profiles stored in the one or more memory modules, wherein each of the one or more fluid profiles comprises information on one or more fluorescent properties of the fluid and visible light transmittance of the fluid; and
determine a fluid type of the fluid based on the comparison.

13. The optical fluid sensor of claim 12, further comprising a first temperature sensor operatively arranged within the chamber to measure a temperature of the fluid disposed in the chamber, and a second temperature sensor operatively arranged in the body to measure a temperature of the light source and the detector.

14. A crossover protection system comprising:
a product transport vehicle comprising a tank compartment for containing a liquid product;
a valve coupled to the tank compartment, the valve regulating a flow of liquid product from the tank compartment and having a normally locked state;
the optical fluid sensor of claim 12 positioned to contact the liquid product stored in the tank compartment;
a tank delivery connector fluidly coupled to a distribution side of the valve, the tank delivery connector comprising a tank tag reader for interrogating a tank tag coupled to a distribution tank separate from the product transport vehicle to retrieve a stored liquid type encoded on the tank tag, wherein the stored liquid type is indicative of a type of the liquid product in the distribution tank; and
a system controller communicatively coupled to the valve, the optical fluid sensor, and the tank delivery connector, the system controller comprising a processor and one or more memory modules communicatively coupled to the processor.

15. A crossover protection system comprising:
a product transport vehicle comprising a tank compartment for containing a liquid product;
a valve coupled to the tank compartment, the valve regulating a flow of liquid product from the tank compartment and having a normally locked state;
an optical fluid sensor positioned to contact the liquid product stored in the tank compartment, the optical fluid sensor comprising:
a body defining a chamber and having one or more apertures to allow the liquid product to enter the chamber;
a light source optically coupled to the chamber and configured to emit IR, UV, and visible light into the chamber;
a detector optically coupled to the chamber and configured to receive light from the chamber;
a processor;
one or more memory modules communicatively coupled to the processor; and
machine readable instructions stored in the one or more memory modules that cause the processor to perform at least the following when executed by the processor:
transmit a control signal to the light source to cause the light source to emit IR light into the chamber;
receive IR light at the detector;
determine that a fluid is present based on the IR light received at the detector;

transmit another control signal to the light source to cause the light source to emit UV light into the chamber to cause the fluid to fluoresce visible light;
receive visible light at the detector; and
determine a fluid type of the fluid in the chamber based on the received visible light;
a tank delivery connector fluidly coupled to a distribution side of the valve, the tank delivery connector comprising a tank tag reader for interrogating a tank tag coupled to a distribution tank separate from the product transport vehicle to retrieve a stored liquid type encoded on the tank tag, wherein the stored liquid type is indicative of a type of the liquid product in the distribution tank; and
a system controller communicatively coupled to the valve, the optical fluid sensor, and the tank delivery connector, the system controller comprising a processor and one or more memory modules.

16. The crossover protection system of claim 15, further comprising machine readable instructions stored in the one or more memory modules that cause the crossover protection system to perform at least the following when executed by the processor:
determine a transported liquid type based on an output from the optical fluid sensor;
receive the stored liquid type signal transmitted by the tank delivery connector;
determine the stored liquid type based on the stored liquid type signal;
compare the transported liquid type to the stored liquid type;
maintain the valve in the normally locked state when the stored liquid type and the transported liquid type do not match to prevent the flow of liquid product from the tank compartment; and
transition the valve from the normally locked state to an unlocked state when the stored liquid type and the transported liquid type match, thereby permitting the flow of liquid product from the tank compartment.

17. The crossover protection system of claim 15, wherein the valve is a control valve.

18. The crossover protection system of claim 15, further comprising a lock mechanism coupled to the tank delivery connector, the lock mechanism comprising a locking lever with a locked position and an unlocked position, the lock mechanism mechanically securing the tank delivery connector to the distribution tank when the locking lever is in the locked position.

19. The crossover protection system of claim 18, further comprising a lock sensor for sensing whether the locking lever is in the locked position or the unlocked position.

20. The crossover protection system of claim 15, wherein power to the tank tag reader is only provided when the locking lever is in the locked position.

21. The crossover protection system of claim 15, wherein the optical fluid sensor further comprises a reflector, wherein the light source and the detector of the optical fluid sensor are positioned at a first side of the chamber and the reflector is positioned at a second side of the chamber, wherein when the liquid product is disposed within the chamber, emitted light from the light source travels through the liquid product in the chamber, reflects off of the reflector, and travels to the detector.

22. An optical fluid sensor comprising:
a body defining a chamber and having one or more apertures to allow a fluid to enter the chamber;
a light source optically coupled to the chamber and configured to emit IR, UV, and visible light into the chamber;
a detector optically coupled to the chamber and configured to receive light from the chamber, wherein the detector measures an intensity of one or more wavelengths of light received by the detector, wherein the light source and the detector are positioned such that, when fluid is disposed within the chamber, emitted light from the light source passes into and through the fluid disposed in the chamber before being received by the detector;
a first temperature sensor operatively arranged within the chamber to measure a temperature of the fluid disposed in the chamber; and
a second temperature sensor operatively arranged in the body to measure a temperature of the light source and the detector.

23. The optical fluid sensor of claim 22, further comprising:
a processor;
one or more memory modules communicatively coupled to the processor; and
machine readable instructions stored in the one or more memory modules that cause the optical fluid sensor to perform at least the following when executed by the processor:
transmit a first control signal to the light source to cause the light source to emit IR light into the chamber;
receive IR light at the detector; and
determine that a fluid is present based on the IR light received at the detector.

24. The optical fluid sensor of claim 22, further comprising:
a processor;
one or more memory modules communicatively coupled to the processor; and
machine readable instructions stored in the one or more memory modules that cause the optical fluid sensor to perform at least the following when executed by the processor:
transmit a control signal to the light source to cause the light source to emit UV light into the chamber in order to cause the fluid to fluoresce visible light;
receive visible light at the detector;
determine a fluid type of the fluid in the chamber based on the visible light received at the detector.

25. The optical fluid sensor of claim 22, further comprising:
a processor;
one or more memory modules communicatively coupled to the processor; and
machine readable instructions stored in the one or more memory modules that cause the optical fluid sensor to perform at least the following when executed by the processor:
transmit a control signal to the light source to cause the light source to emit visible light into the chamber;
receive visible light at the detector;
determine a fluid type of the fluid in the chamber based on the visible light received at the detector.

26. A crossover protection system comprising:
a product transport vehicle comprising a tank compartment for containing a liquid product;
a valve coupled to the tank compartment, the valve regulating a flow of liquid product from the tank compartment and having a normally locked state;

the optical fluid sensor of claim 22 positioned to contact the liquid product stored in the tank compartment;

a tank delivery connector fluidly coupled to a distribution side of the valve, the tank delivery connector comprising a tank tag reader for interrogating a tank tag coupled to a distribution tank separate from the product transport vehicle to retrieve a stored liquid type encoded on the tank tag, wherein the stored liquid type is indicative of a type of the liquid product in the distribution tank; and a system controller communicatively coupled to the valve, the optical fluid sensor, and the tank delivery connector, the system controller comprising a processor and one or more memory modules communicatively coupled to the processor.

* * * * *